United States Patent
Huang et al.

(10) Patent No.: US 10,231,707 B2
(45) Date of Patent: Mar. 19, 2019

(54) ULTRASOUND WAVEFORM TOMOGRAPHY WITH WAVE-ENERGY-BASED PRECONDITIONING

(71) Applicant: LOS ALAMOS NATIONAL SECURITY, LLC, Los Alamos, NM (US)

(72) Inventors: Lianjie Huang, Los Alamos, NM (US); Zhigang Zhang, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 915 days.

(21) Appl. No.: 14/339,759

(22) Filed: Jul. 24, 2014

(65) Prior Publication Data
US 2015/0025388 A1 Jan. 22, 2015

Related U.S. Application Data

(63) Continuation of application No. PCT/US2013/024656, filed on Feb. 4, 2013.
(Continued)

(51) Int. Cl.
*A61B 5/00* (2006.01)
*A61B 8/00* (2006.01)
(Continued)

(52) U.S. Cl.
CPC .......... *A61B 8/5207* (2013.01); *A61B 5/0073* (2013.01); *A61B 5/7275* (2013.01); *A61B 8/085* (2013.01); *A61B 8/0825* (2013.01); *A61B 8/13* (2013.01); *A61B 8/14* (2013.01); *A61B 8/145* (2013.01); *A61B 8/15* (2013.01);
(Continued)

(58) Field of Classification Search
None
See application file for complete search history.

(56) References Cited

U.S. PATENT DOCUMENTS 4,075,883 A 2/1978 Glover
4,582,065 A 4/1986 Adams
(Continued)

FOREIGN PATENT DOCUMENTS

JP 2009189867 A 8/2009
KR 1020100075011 A 7/2010
(Continued)

OTHER PUBLICATIONS

Fichtner et al. ("Full Seismic Waveform Tomography for upper-mantle structure in the Australasian region using Adjoint Methods", Geophys. J. Int. (2009) 179, pp. 1703-1725).*
(Continued)

*Primary Examiner* — Michael J Carey
*Assistant Examiner* — Farouk A Bruce
(74) *Attorney, Agent, or Firm* — Lewis Roca Rothgerber Christie LLP

(57) ABSTRACT

Synthetic-aperture ultrasound tomography systems and methods using scanning arrays and algorithms configured to simultaneously acquire ultrasound transmission and reflection data, and process the data using ultrasound waveform tomography with a wave-energy-based preconditioning method for improved ultrasound tomography imaging.

17 Claims, 20 Drawing Sheets

Related U.S. Application Data

(60) Provisional application No. 61/594,865, filed on Feb. 3, 2012.

(51) Int. Cl.

| | | |
|---|---|---|
| *A61B 8/13* | (2006.01) | |
| *A61B 8/14* | (2006.01) | |
| *A61B 8/15* | (2006.01) | |
| *A61B 8/08* | (2006.01) | |
| *G01S 15/89* | (2006.01) | |
| *G06T 5/00* | (2006.01) | |
| *G06T 11/00* | (2006.01) | |

(52) U.S. Cl.
CPC ............ *A61B 8/406* (2013.01); *A61B 8/4477* (2013.01); *A61B 8/4488* (2013.01); *A61B 8/4494* (2013.01); *A61B 8/483* (2013.01); *G01S 15/8915* (2013.01); *G01S 15/8929* (2013.01); *G01S 15/8997* (2013.01); *G06T 5/001* (2013.01); *G06T 11/005* (2013.01)

(56) References Cited

U.S. PATENT DOCUMENTS

| | | | |
|---|---|---|---|
| 5,465,722 | A | 11/1995 | Fort et al. |
| 5,908,390 | A | 6/1999 | Matsushima |
| 6,186,951 | B1 | 2/2001 | Lizzi et al. |
| 2001/0020130 | A1 | 9/2001 | Gee et al. |
| 2002/0099290 | A1 | 7/2002 | Haddad |
| 2002/0173722 | A1 | 11/2002 | Hoctor |
| 2003/0158481 | A1 | 8/2003 | Stotzka |
| 2004/0034307 | A1 | 2/2004 | Johnson et al. |
| 2006/0058678 | A1 | 3/2006 | Vitek |
| 2006/0173304 | A1 | 8/2006 | Wang |
| 2006/0184020 | A1 | 8/2006 | Sumi |
| 2006/0293597 | A1 | 12/2006 | Johnson et al. |
| 2007/0100239 | A1 | 5/2007 | Nair et al. |
| 2008/0045864 | A1 | 2/2008 | Candy et al. |
| 2008/0081993 | A1 | 4/2008 | Waki |
| 2008/0229832 | A1 | 9/2008 | Huang |
| 2008/0294043 | A1* | 11/2008 | Johnson ............... A61B 8/0825 600/437 |
| 2008/0319318 | A1 | 12/2008 | Johnson et al. |
| 2009/0076389 | A1 | 3/2009 | Jin et al. |
| 2009/0099456 | A1 | 4/2009 | Burcher et al. |
| 2010/0157732 | A1 | 6/2010 | Saenger et al. |
| 2011/0118984 | A1 | 5/2011 | Chevion et al. |
| 2011/0125014 | A1 | 5/2011 | Derode et al. |
| 2011/0131020 | A1* | 6/2011 | Meng ..................... G01V 1/303 703/2 |

FOREIGN PATENT DOCUMENTS

| | | | |
|---|---|---|---|
| WO | 2007133882 | A2 | 11/2007 |
| WO | 2011103303 | A2 | 8/2011 |

OTHER PUBLICATIONS

Sallard et al. ("Use of a priori Information for the Deconvolution of Ultrasonic Signals", Rev. of Prog. in Quantitative Nondestructive Evaluation, vol. 17 Plenum Press, New York, 1998, pp. 735-742).*
Tape et al. ("Finite-Frequency Tomography Using Adjoint Methods-Methodology and Examples Using Membrane Surface Waves", Geophys. J. Int. (2007) 168, pp. 1105-1129).*
Yao et al., "Application and Study on Preconditioned Conjugate Gradient Method Algorithm in Concrete Ultrasonic Computerized Tomography," 2010 Second International Conference on Information Technology and Computer Science, Kiev, 2010, pp. 348-352.*
Rivaz et al. (Ultrasound Elastography: A Dynamic Programming Approach, IEEE Transactions on Medical Imaging, vol. 27, No. 10, Oct. 2008, pp. 1373-.1377).*
Cuiping, Li et al., "In Vivo Breast Sound-Speed Imaging with Ultrasound Tomography", Ultrasound in Medicine & Biology, Oct. 2009, vol. 35, No. 10, pp. 1616-1628.
Korean Intellectual Property Office (KIPO), International Search Report and Written Opinion dated Jun. 2, 2013, PCT International Application No. PCT/US2013/024676, pp. 1-10, with claims searched, pp. 11-18.
Korean Intellectual Property Office (KIPO), International Search Report and Written Opinion dated May 30, 2013, PCT International Application No. PCT/US2013/024545, pp. 1-12, with claims searched, pp. 13-20.
Korean Intellectual Property Office (KIPO), International Search Report and Written Opinion dated May 30, 2013, Counterpart PCT International Application No. PCT/US2013/024656, pp. 1-10, with claims searched, pp. 11-16.
Korean Intellectual Property Office (KIPO), International Search Report and Written Opinion dated May 30, 2013, PCT International Application No. PCT/US2013/024662, pp. 1-10, with claims searched, pp. 11-19.
Korean Intellectual Property Office (KIPO), International Search Report and Written Opinion dated May 30, 2013, PCT International Application No. PCT/US0213/024539, pp. 1-16, with claims searched, pp. 17-24.
Office action dated May 9, 2017 issued in co-pending U.S. Appl. No. 14/339,780.
Office action dated Mar. 31, 2017 issued in co-pending U.S. Appl. No. 14/339,712.
Office action dated Apr. 4, 2017 issued in co-pending U.S. Appl. No. 14/339,738.
Office action dated May 10, 2017 issued in co-pending U.S. Appl. No. 14/339,791.
Office action dated May 2, 2017 issued in co-pending U.S. Appl. No. 14/339,728.
Office action dated Apr. 19, 2017 issued in co-pending U.S. Appl. No. 14/339,770.
Anagaw et al., "Full Waveform Inversion with Total Variation Regularization," Recovery—2011 CSPG CSEG CWLS Convention, pp. 1-4.
Cobbold, (2007), Foundations of Biomedical Ultrasound, New York: Oxford University Press, pp. 110-111.
Devaney et al. Super-resolution Processing of Multi-Static Data Using Time Reversal and Music, 2000. {Online]: http://www.ece.neu.edu/faculty/devaney/ajd/preprints.htm, pp. 4,10.
Devaney et al., Time-reversal-based imaging and inverse scattering of multiply scattering point targets, 2005, The Journal of the Acoustical Society of America, vol. 118, No. 5, p. 3132.
Duric et al. "Development of Ultrasound Tomography for Breast Imaging: Technical Assessment," Medical Physics 32(5):1375-86.
Huang et al., "A Rapid and Robust Numerical Algorithm for Sensitivity Encoding with Sparsity Constraints: Self-Feeding Sparse SENSE," Magnetic Resonance in Medicine, 2010, 64:1078-1088.
Ikedo et al., Development of a fully automatic scheme for detection of masses in whole breast ultrasound images, 2007, Medical Physics, vol. 24, No. 11, pp. 4381.
Labyed et al., Ultrasound Time-Reversal Music Imaging with Diffraction and Attenuation Compensation, 2012, IEEE Transactions on Ultrasonics, Ferroelectrics, and Frequency Control, vol. 59, No. 10, p. 2188.
Lemoult et al., Time Reversal in Subwavelength-Scaled Resonant Media: Beating the Diffraction Limit, 2011, International Journal of Microwave Science and Technology, vol. 2011, Article ID 425710, p. 4.
Nguyen et al., The DORT solution acoustic inverse scattering problem of a small elastic scatterer, 2010, Ultrasonics, col. 50, Issue 8, pp. 831-832.
Sumi, C., "Spatially variant regularization for the Deconvolution of Ultrasonic Signals," Rev. of Prog. in Quantitative Nondestructive Evaluation, J Med Ultrasonics (2007) 34:125-131, Mar. 8, 2007.
Szabo et al. 2004, "Determining the pulse-echo electromechanical characteristic of a transducer using flat plates and point targets," The Journal of the Acoustical Society of America, vol. 116, No. 1, p. 91.

(56) References Cited

OTHER PUBLICATIONS

Tai, et al. "Image Denoising Using TV-Stokes Equation with an Orientation-Matching Minimization" Space and Variational Methods in Computer Vision, Lecture Notes in Computer Science, vol. 5567, 2009, pp. 1-12.

Waag et al., A Ring Transducer System for Medical Ultrasound Research, 2006, IEEE Transactions on Ultrasonics, Ferroelectrics, and Frequency control, vol. 53, No. 10, p. 1709.

Yao et al., "A Fast Algorithm to Calculate Ultrasound Pressure Fields from Single-Element Transducers," 1989, IEEE Transactions on Ultrasonics, Ferroelectrics and Frequency Control, vol. 36, No. 4, pp. 446.

Korean Intellectual Property Office (KIPO), International Search Report and Written Opinion dated May 30, 2013, Counterpart PCT International Application No. PCT/US2013/024512, pp. 1-10, with claims searched, pp. 11-21.

Korean Intellectual Property Office (KIPO), International Search Report and Written Opinion dated May 30, 2013, PCT International Application No. PCT/US 2013/024550, pp. 1-11, with claims searched, pp. 12-21.

\* cited by examiner

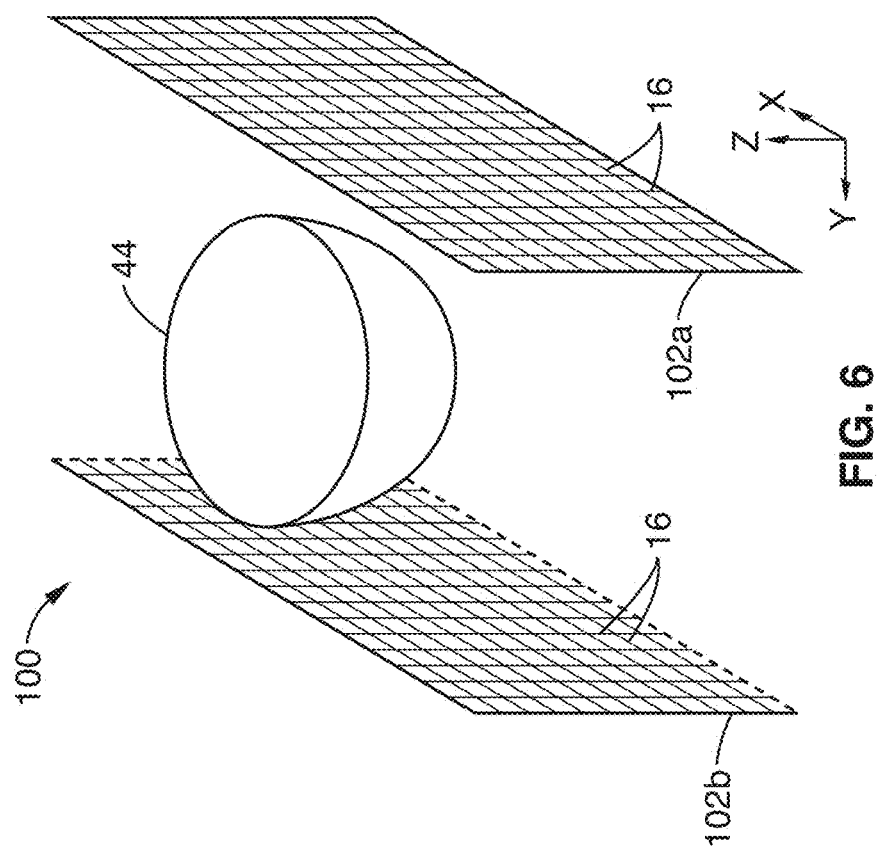
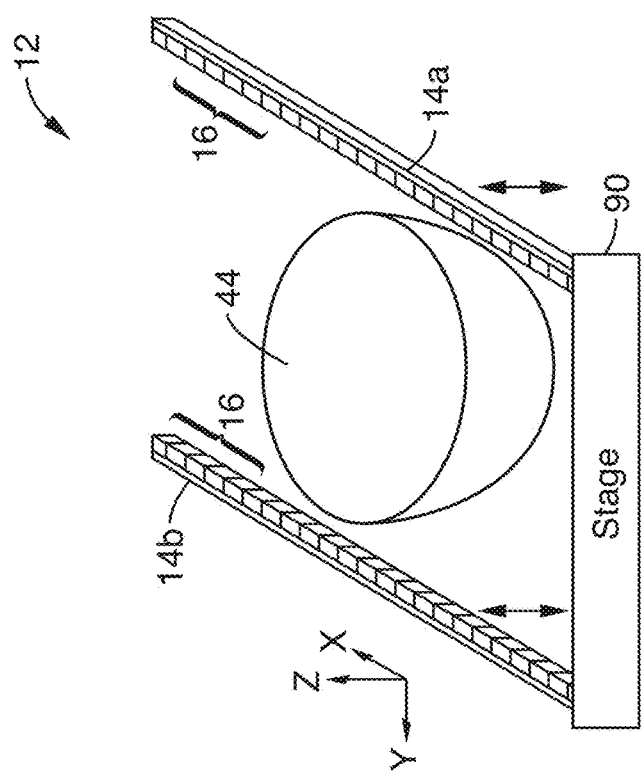
FIG. 6
FIG. 5

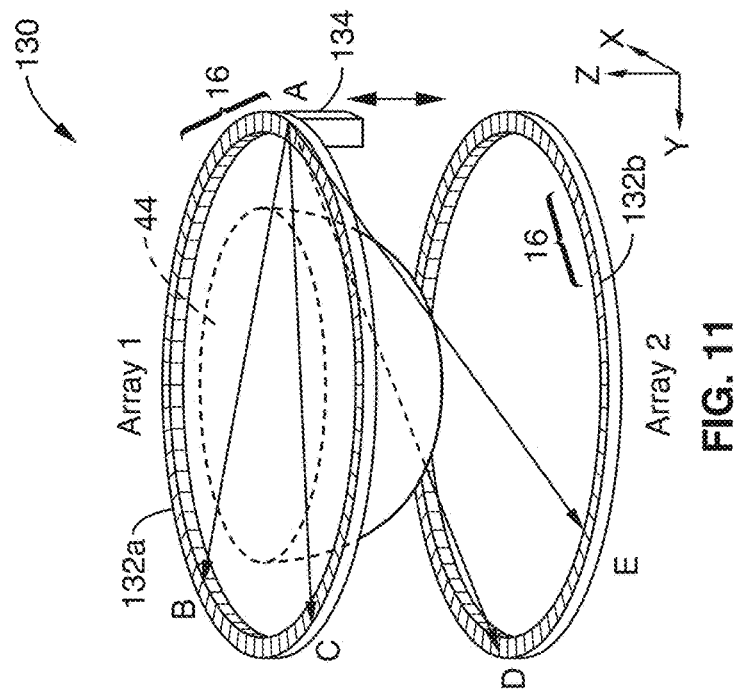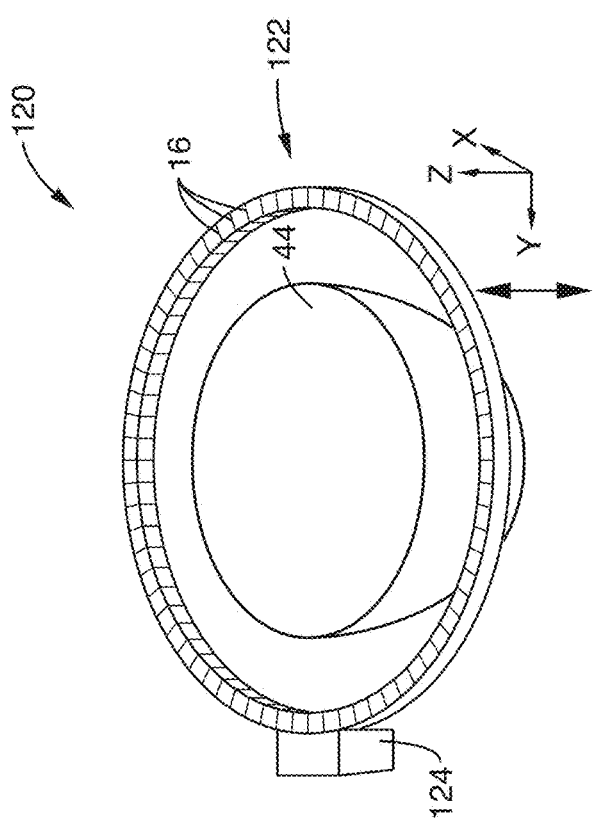

ULTRASOUND WAVEFORM TOMOGRAPHY WITH WAVE-ENERGY-BASED PRECONDITIONING

CROSS-REFERENCE TO RELATED APPLICATIONS

This application is a 35 U.S.C. § 111(a) continuation of PCT international application number PCT/US2013/024656 filed on Feb. 4, 2013, incorporated herein by reference in its entirety, which claims priority to, and the benefit of, U.S. provisional patent application Ser. No. 61/594,865, filed on Feb. 3, 2012, incorporated herein by reference in its entirety. Priority is claimed to each of the foregoing applications.

The above-referenced PCT international application was published as PCT International Publication No. WO 2013/116851 on Aug. 8, 2013, incorporated herein by reference in its entirety.

STATEMENT REGARDING FEDERALLY SPONSORED RESEARCH OR DEVELOPMENT

This invention was made with Government support under Grant No. MIPR0LDATM0144 from the Breast Cancer Research Program of DoD-Congressionally Directed Medical Research Programs and Contract No. DE-AC52-06NA25396 awarded by the Department of Energy. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to imaging, and more particularly to ultrasound imaging using a synthetic aperture ultrasound ray tomography and ultrasound waveform tomography.

2. Description of Related Art

Breast cancer is the second-leading cause of cancer death among American women. The breast cancer mortality rate in the U.S. has been flat for many decades, and has decreased only about 20% since the 1990s. Early detection is the key to reducing breast cancer mortality. There is an urgent need to improve the efficacy of breast cancer screening. Ultrasound tomography is a promising, quantitative imaging modality for early detection and diagnosis of breast tumors.

Ultrasound waveform tomography is gaining popularity, but is computationally expensive, even for today's fastest computers. The computational cost increases linearly with the number of transmitting sources.

Synthetic-aperture ultrasound has great potential to significantly improve medical ultrasound imaging. In a synthetic aperture ultrasound system, ultrasound from each element of a transducer array propagates to the entire imaging domain, and all elements in the transducer array receive scattered signals.

Many conventional ultrasound systems record only 180° backscattered signals. Others are configured to receive only transmission data from the scanning arrays. Accordingly, these systems suffer from extensive computational costs, insufficient resolution, or both.

It is difficult to reconstruct the region far away from an ultrasound transducer array when using reflection data for ultrasound waveform tomography. The geometrical spreading is the primary cause of this problem. The defocusing effect in synthetic-aperture ultrasound is stronger in the region far away from a transducer array than the region close to the transducer array. This defocusing effect may play a role in ultrasound waveform tomography using reflection data.

Preconditioning the gradients has been introduced to accelerate the convergence of waveform inversion. It has been shown that the diagonal terms of the approximate Hessian is a zero-lag correlation of the scattered waves, which represent the geometrical spreading effects as the scattering points move away from the sources and receivers. It has been suggested to scale the gradient by the diagonal terms of the approximate Hessian. However, it is generally expensive to calculate Jacobin matrix. One method is to replace the zero-lag autocorrelation of Green's functions by a pseudo-Hessian matrix. This approach reduces the computational cost by assuming that the zero-lag autocorrelations of the Green's functions are the same. Others have introduced a different pseudo-Hessian matrix using the amplitude of impulse responses from the sources to approximate the zero-lag autocorrelations.

BRIEF SUMMARY OF THE INVENTION

The system and method of the present invention uses ultrasound data acquired using a synthetic-aperture ultrasound system. The investigational synthetic-aperture ultrasound tomography system of the present invention allows acquisition of each tomographic slice of patient ultrasound data in real time. In the system, each element of the transducer array transmits ultrasound sequentially, and elements in the transducer array simultaneously record ultrasound signals scattered from the tissue after each element is fired. The features of the system and method of the present invention provide a real-time synthetic-aperture system that can be used for patient data acquisition.

In the synthetic-aperture ultrasound tomography system of the present invention, ultrasound from each element of a transducer array or a virtual source of multiple elements propagates to the entire imaging domain, and all elements in the transducer array receive ultrasound signals reflected/scattered from the imaging region and/or transmitted/scattered through the imaging region. Therefore, the acquired synthetic-aperture ultrasound data contain information of ultrasound reflected/scattered and transmitted from all possible directions from the imaging domain to the transducer array to generate a more accurate, 3-D, high resolution image, while minimizing computational costs of the system.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 5 illustrates a schematic view of a two parallel-bar ultrasound transducer array scanner.

FIG. 6 illustrates a schematic view of a scanner comprising two parallel planar arrays.

FIG. 10 shows a schematic view of a torroidal array scanner having a a circular array of transducers.

FIG. 11 shows a schematic view of a synthetic-aperture ultrasound breast tomography scanner that incorporates use of two circular transducer arrays.

DETAILED DESCRIPTION OF THE INVENTION

The description below is directed to synthetic aperture ultrasound tomography systems for imaging a medium such as patient tissue, along with ultrasound waveform tomography methods for acquiring and processing data acquired from these systems, or other systems that may or may not be available in the art.

The synthetic-aperture breast ultrasound tomography system of the present invention uses synthetic-aperture ultrasound to obtain quantitative values of mechanical properties of breast tissues. In this system, each transducer element transmits ultrasound waves sequentially, and when an ultrasound transducer element transmits ultrasound waves propagating through the breast, all ultrasound transducer elements (at least within a portion of an array) simultaneously receive ultrasound reflection/transmission, or forward and backward scattering signals. The ultrasound reflection/transmission signals are used to obtain quantitative values of mechanical properties of tissue features (and in particular breast tumors), including the sound speed, density, and attenuation.

While the systems and methods described below are particularly directed and illustrated for imaging of breast tissues, it is appreciated that the systems and methods may also be employed for waveform tomography on other tissues or scanning mediums.

I. Synthetic Aperture Ultrasound Tomography System

Figure 1:
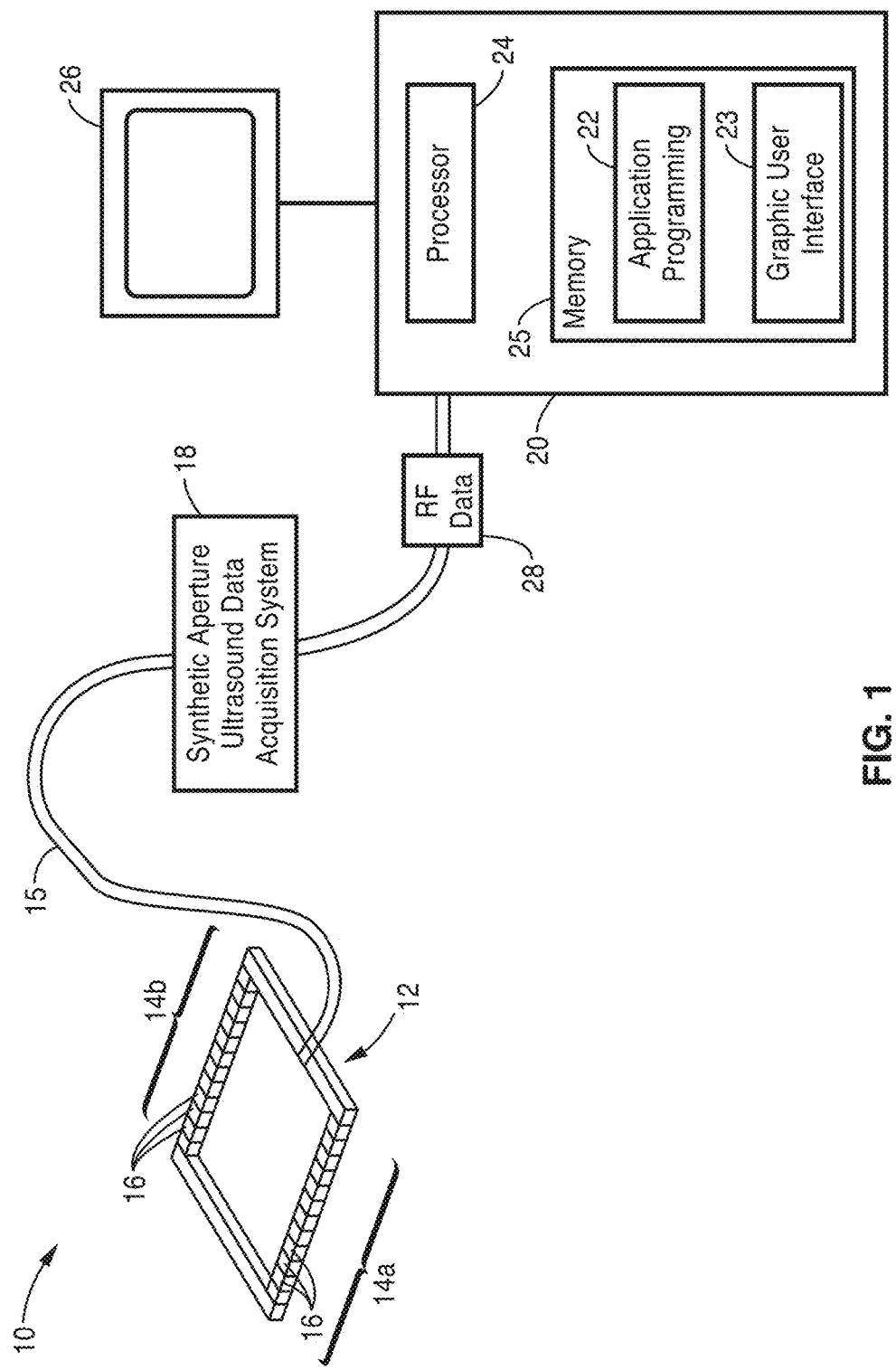
FIG. 1 is a schematic diagram of a synthetic-aperture ultrasound system in accordance with the present invention.

FIG. 1 is a schematic diagram of a synthetic-aperture ultrasound system 10 in accordance with the present invention. The system 10 includes a scanner 12 comprising a plurality of individual transducer elements 16 disposed within one or more arrays (e.g. the opposing parallel arrays 14a and 14b shown in FIG. 1). The scanner 12 is coupled to a server or like computing apparatus 20 (e.g. with a cable 15 or other connection means such as, but not limited to, a wireless connections means) and synthetic aperture ultrasound data acquisition system 18 that outputs RF data 28 corresponding to readings acquired by the scanner 12.

The computer 20 comprises a processor 24 configured to operate one or more application programs 22 located within memory 25, wherein the application programs 22 may contain one or more algorithms or methods of the present invention for imaging a tissue medium for display via a graphical user interface 23 on monitor 26, or other means. For example, the application programming 22 may comprise the programming configured for operating the sequential excitation method 50 shown in FIG. 4 or ultrasound waveform tomography imaging method 200 shown in FIG. 14. The computer 20 controls ultrasound tomography data acquisition, and the process is completed automatically. The whole-breast scanning time with approximately 100 slides takes approximately 2 minutes.

Figure 2:
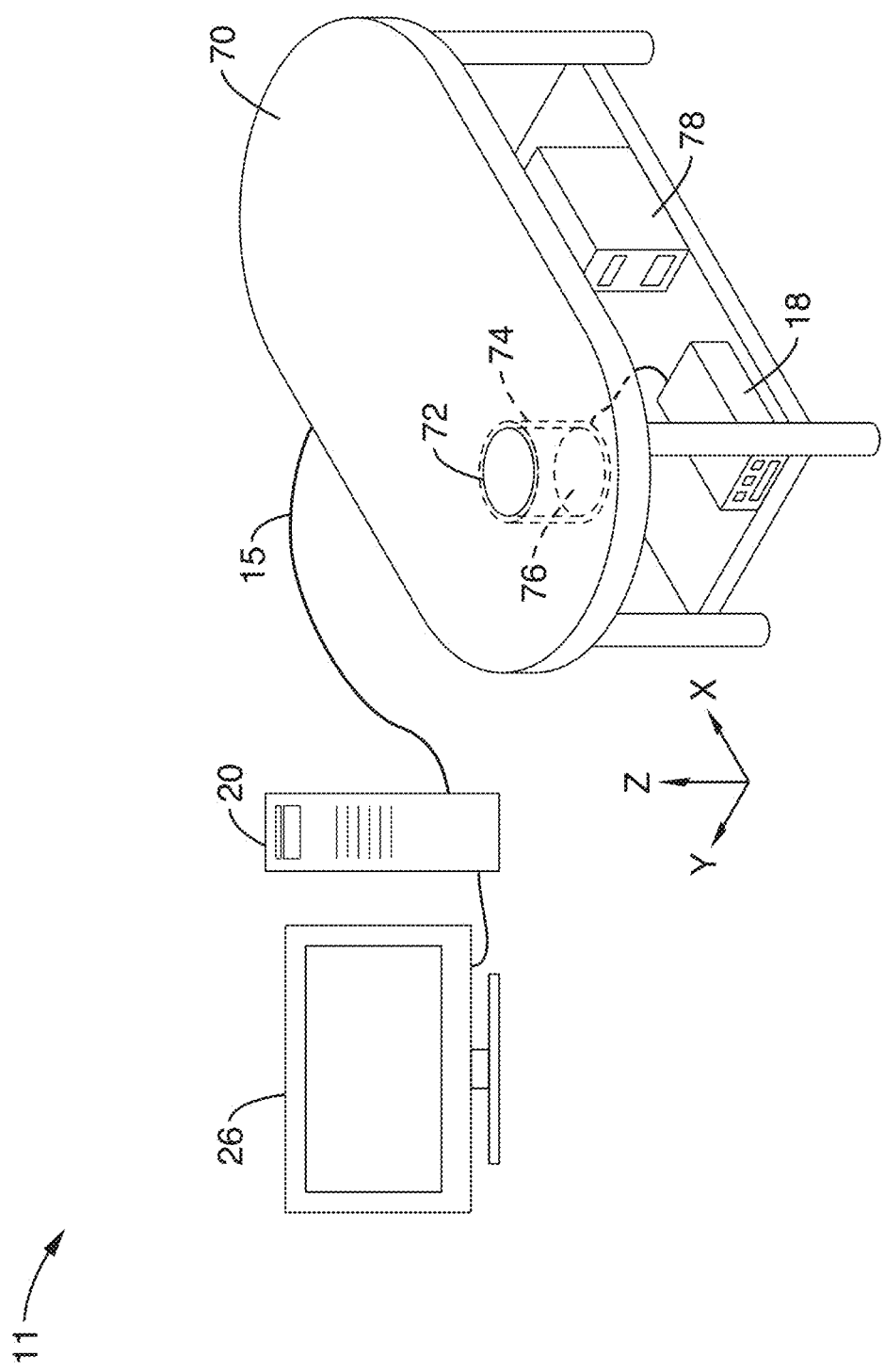
FIG. 2 is a schematic diagram of a synthetic-aperture ultrasound tomography system for scanning breast tissue in accordance with the present invention

FIG. 2 is a schematic view of a breast ultrasound tomography system 11 in accordance with the present invention. System 11 includes a table 70 having a water tank 76 with an open aperture at the top of the table 70 for insertion of the patient's breast tissue (which ideally hangs pendant within water tank 76 during imaging). Tank 76 includes one or more synthetic-aperture ultrasound transducer arrays 74 located within one or more surfaces of the tank. The transducer array(s) 74 are immersed within the water tank 76 configured for receiving the patients breast 44 through aperture 72, and scanning the breast 44 while the patient is lying down on the table 70 in the prone position. As described in further detail below, transducer array(s) 74 may comprise a number of different configurations, with the water tank housing 76 shaped accordingly to house the array(s) 74. The water tank housing 76 material preferably comprises a light, non-conductive material that conforms to the shape of the array(s) 74 (e.g. rectangular for 2-parallel bar array scanner 12 of FIG. 1, or cylindrical for the scanners 110, 120 and 130 shown in FIG. 7, FIG. 10 and FIG. 11, respectively).

Positioning of the active areas of all array(s) 74 relative to the water tank housing 76 is preferably aligned such that the ultrasound energy for the transducer elements 16 (FIG. 1) is focused onto the same plane perpendicular to the housing (for parallel bar scanner 12 (FIG. 5) or planar 100 (FIG. 6) arrays). The arrays (e.g. arrays 14a and 14b, FIG. 1) are preferably electrically isolated and grounded.

The system 11 includes a data acquisition system 18 that may be coupled to a computer system or electronics 78 that control scanning. The data acquisition system 18 may also be coupled to a computer 20 for running application programming 22 (FIG. 1) to perform tomography reconstructions.

During the ultrasound data acquisition in the synthetic-aperture ultrasound tomography system 10, the raw ultrasound data 28 (radio-frequency data) may be first stored within computer memory 25 (FIG. 1) (which may comprise solid state drives or other storage means available in the art), allowing real-time patient data acquisition for clinical applications.

Figure 3:
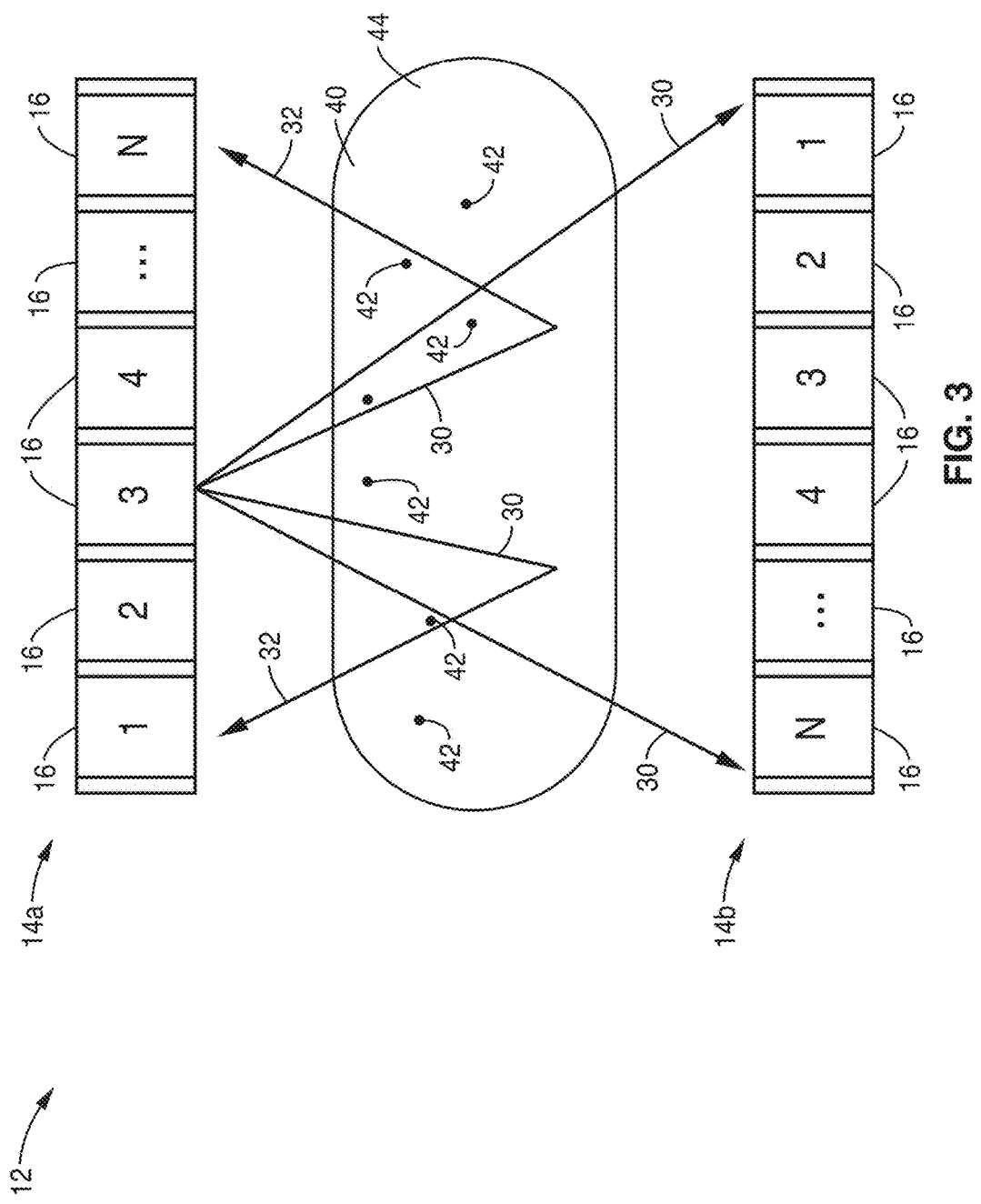
FIG. 3 is a schematic diagram of the scanner of the ultrasound tomography system of FIG. 1 interrogating a region of tissue.

FIG. 3 is a schematic diagram of the two parallel bar arrays 14a and 14b of scanner 12 of FIG. 1 shown interrogating a region of tissue 44 (e.g. breast tissue for mammography) in accordance with a preferred method of the present invention. The ultrasound imaging system 10 focuses an array 14a and 14b of N transducers 16 acting in a transmit-receive mode. Each element of the array 14a 14b is excited sequentially (e.g. transducer 3 of array 14a is shown in excitation mode) to generate an ultrasound field or signal 30 through the tissue surface 40 and into tissue medium 44 having a plurality of point scatterers 42. The backscattered signals 32 are measured in parallel by all N elements 16. In addition, opposing array 14b transducers are positioned facing array 14a such that one or more elements of the array 14b receive direct transmission signals 30 simultaneously with reception of backscatter or reflection signals 32 being received by array 14a.

Figure 4:
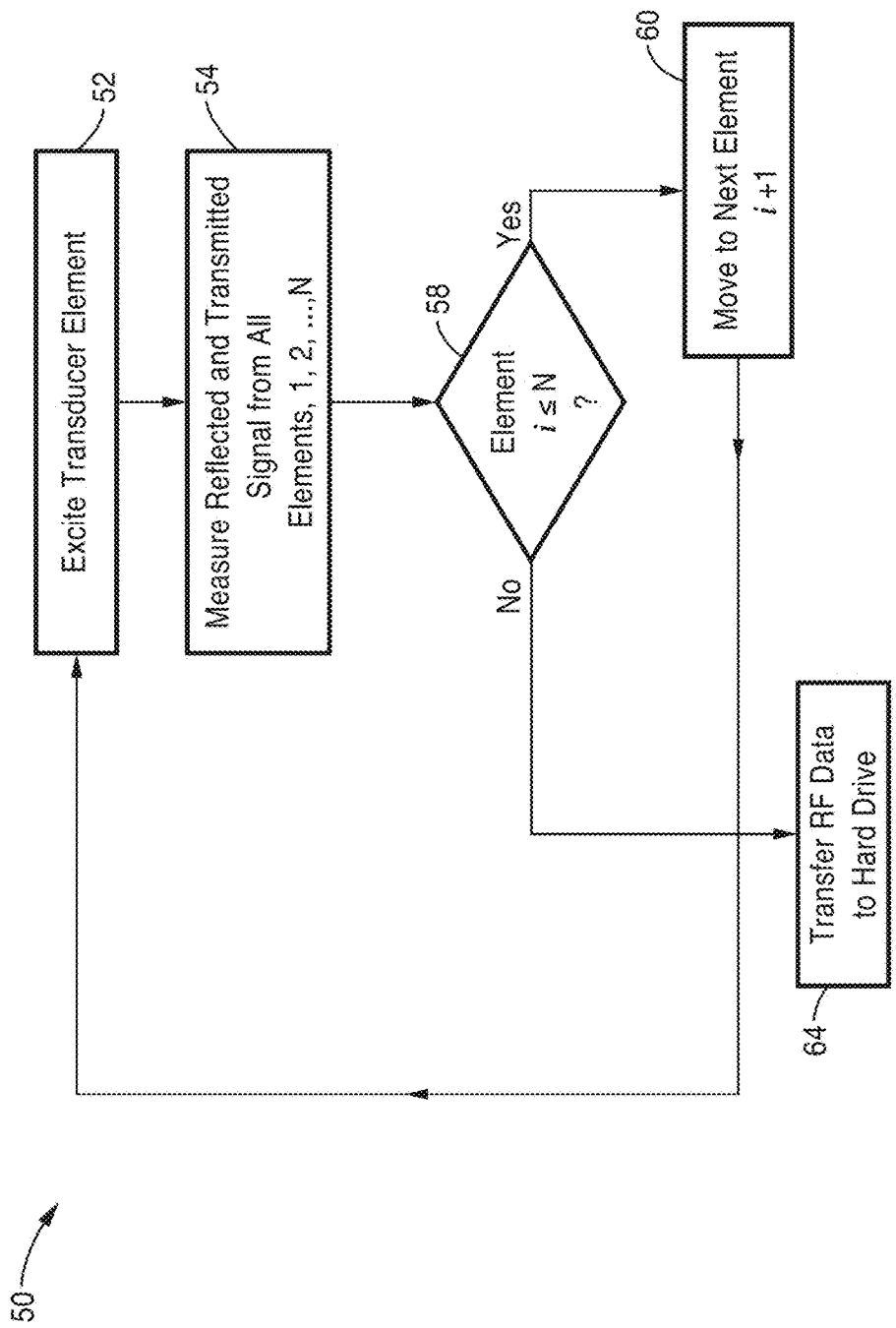
FIG. 4 shows flow diagram of a method for sequentially exciting a region of tissue and acquiring reflection and transmission data in accordance with the present invention.

FIG. 4 shows flow diagram of a method 50 for sequentially exciting a region of tissue 44 in accordance with the present invention. At step 52, a first element (e.g. element 1 or i) of array 14a 14b of N ultrasound transducer elements 16 is excited for interrogating an inhomogeneous medium 44. At step 54, the backscattered/reflected signals 32 are received/measured by all elements 16 (of at least 14a), while transmission signals 30 are received/measured by one or more elements 16 of array 14b. At step 58, the method evaluates whether all the elements 16 in the arrays 14a and 14b have been excited (and imaged). If the last element in the arrays 14a, 14b has not been reached, the method moves to the next element 16 in the array (14a or 14b) at step 60, and repeats the process sequentially until the $N^{th}$ element is reached. At this point, the individual reflection/transmission data are RF data, and the process 50 transfers the RF data to memory or solid state drives 25 at step 64.

In the phased transducer arrays for synthetic-aperture breast ultrasound tomography, a plurality of transducer elements 16 are fired with different delayed times to simulate ultrasound waves emerging from a virtual point source. The systems and methods of the present invention preferably use the virtual point sources of the synthetic-aperture breast ultrasound tomography system to improve signal-to-noise ratios of breast ultrasound data.

The various scanning arrays invention, described below with reference to FIG. 5 through FIG. 7 and FIG. 10 through FIG. 13, are shown to illustrate that the systems 10, 11 and methods 50, 200 may be achieved in various configurations. Yet, the scanning arrays of FIG. 5 through FIG. 7 and FIG. 10 through FIG. 13 all share at least one common characteristic in that at a plurality of transducers 16 of an array, or portion of an array, oppose (at a spaced-apart distance across the target scanning medium 44) a plurality of transducers 16 of either another portion of the array, or a separate array, so that reflection and transmission data may be acquired with each successive transducer excitation. The following are specific examples of arrays that may be used in the systems 10, 11 and methods 50, 200 of the present invention. However, other configurations are contemplated. In each of these configurations, the scanner 74 is shown without table 70 or housing 76 for clarity.

A. Dual Parallel-Bar Array Scanner

FIG. 5 illustrates a two parallel-bar ultrasound transducer array scanner 12, which is illustrated in reference to implementation within system 10 in FIG. 1, and schematically in operation as a synthetic-aperture scanner in FIG. 3.

As shown in FIG. 5, the two arrays 14a and 14b are shown in opposing orientation (e.g facing each other and matching in location along x-axis in FIG. 5), and positioned in the x-y plane (preferrably parallel to table 70 in FIG. 2, such that they are spaced-apart across the scanning region 44. Each of the 14a and 14b comprises a plurality of N transducers 16 (e.g. count of 128) linearly aligned in series (shown in along the x-axis for reference) as parallel-phased arrays firing toward each other in operation (see FIG. 3).

A robotic stage 90 is provided so that the arrays can move in unison vertically along the z-axis to scan the tissue 44. The transducer arrays 14a and 14b are configured to scan the breast 44 from the chest wall to the nipple region, slice by slice. To image the axillary region (region of breast closest to the armpit of the patient, not shown), the two transducer arrays 14a and 14b can be steered toward the axillary region, with one of the transducer arrays placed near the axillary region. The axillary region, or basin, is important to oncologic surgeons, as it represents the principal lymphatic drainage region of the breast. Lymphatic metastasis from a malignant breast lesion will most often occur in this region.

Arrays 14a and 14b may also be translated (either in concert, or with respect to each other) in the x and y axes to closely conform to varying patient anatomy.

Figure 8:
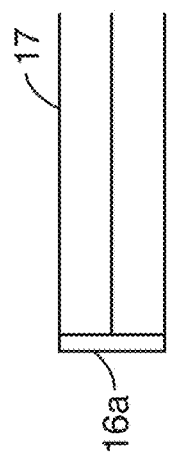
FIG. 8 shows a flat transducer configured to generate a collimated beam.
Figure 9:
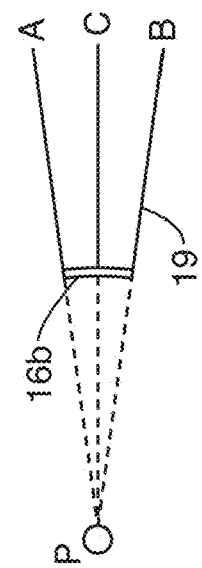
FIG. 9 shows an arcuate transducer configured to generate a diverging beam.

Referring to FIG. 8 and FIG. 9, the transducer 16 may either be flat or circular, and the surface of the transducer element 16 may either be flat, as in transducer 16a in FIG. 8, or arcuate in shape, as shown in transducer 16b of FIG. 9. The flat transducer 16a of FIG. 8 generates a collimated beam 17, whereas the curvilinear transducer 16b of FIG. 9 has a focal point P that is behind the emitting surface to generate a diverging beam 19 (defocused or lens configuration preferably in the y-z plane) across a field of view from A to B (centered on C). The curvilinear transducer 16b of FIG. 9 helps get a 3-D volume while scanning, and is particularly useful with line arrays such as those in FIG. 5, FIG. 10, FIG. 11, and FIG. 13.

In one embodiment, exemplary dimensions for the arrays 14a and 14b and transducers 16 are as follows: a length inside the water tank along X-axis (the horizontal direction) of 16 inches, with 19.2 inches along Y-axis (the horizontal direction) and 16 inches in height along Z-axis (the vertical direction). The distances from the ends of the ultrasound phased transducer arrays 14a and 14b to the inside walls of the water tank along X-axis are approximately 3.8425 inches. In one embodiment, the horizontal distance between the front surfaces of the two parallel phased ultrasound transducer arrays can be adjusted from 12 cm to 25 cm, with a 1 cm increment utilizing 14 different sets of spacer blocks. The accuracy and precision of the horizontal position is ideally 5 microns or better. The vertical travel (Z axis) of the two parallel ultrasound phased transducer arrays 14a and 14b is 10 inches from the top surface of the water level. The vertical travel step interval can be adjusted to any value, such as 0.25 mm, 0.5 mm, 1 mm, and 2 mm.

In one embodiment, array 14a, 14b parameters are as follows: center frequency of 1.5 MHz, bandwidth of ~80% bandwidth (−6 dB) (measured for two-way sound propagation energy), the open angle of ultrasound waves emitting from a single element at ~80°, with uniform transducer elements 16 (<1 dB variation, and uniform bandwidth for one-way sound propagation energy).

In one embodiment, the arrays 14a, 14b comprise 1.5 MHz arrays with 384 elements each, equally spaced along the array. In one example, the dimensions/characteristics of the transducer elements are as follows: elevation aperture: 15 mm, element width: 0.4 mm for 1.5 MHz arrays, elevation focus: 10 cm away from the transducer element, with all transducers configured to be aligned along the array and perpendicular to the elevation plane.

It is appreciated that the above dimensions and configuration details are for reference purposes only, and such characteristics may be varied accordingly.

The advantage of the configuration of scanner 12, over, e.g. the planar arrays of FIG. 6, is that the system 10 is using a fewer number of transducer elements.

B. Dual Parallel Planar Array Scanner

FIG. 6 illustrates a scanner 100 comprising two parallel planar arrays 102a and 102b aligned opposing each other across the scanning medium 44. Arrays 102a and 102b each comprise matching grids of 2-D arrays of transducers 16 (e.g. transducers 16 share the same locations in their respective x-z planes shown in FIG. 6). With the planar arrays the scanner 100 generally does not need to be translated in the z (vertical) direction.

There are generally two limitations for the synthetic-aperture breast ultrasound tomography with the cylindrical or circular transducer arrays: (a) it is difficult to image the axillary region of the tissue 44; and (b) one size of the cylindrical or circular transducer array will either be undersized or oversized for most sizes of the breast.

Synthetic-aperture breast ultrasound tomography with two parallel planar ultrasound transducer arrays 102a and 102b can overcome these two limitations. As shown in FIG. 6, one planar/2D transducer array 102b can be placed close to the axillary region of the tissue 44. In addition, the distance between the two planar ultrasound transducer arrays 102a and 102b can be adjusted with respect to each other (either manually or with robotic stage 90 as shown in FIG. 5) to fit different sizes of the breast. The ultrasound transducer elements 16 can be in circular or rectangular shape, and the surface of the transducer element can be either flat or arc-shaped, as shown in FIG. 8 and FIG. 9.

C. Cylindrical Array Scanner

Figure 7:
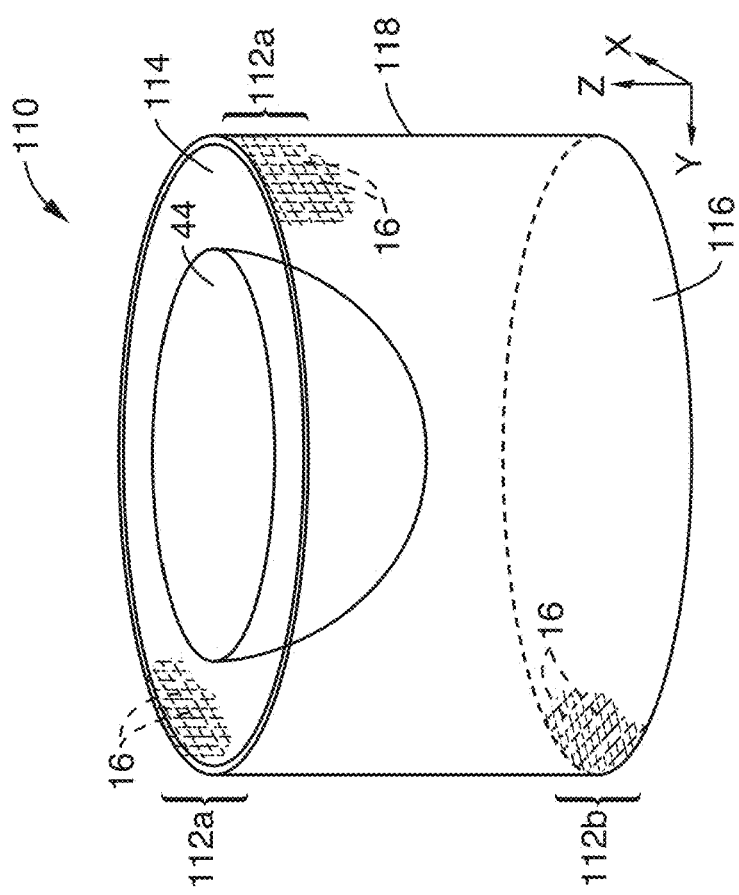
FIG. 7 shows a schematic view of a cylindrical array scanner having a cylindral 2-D array of transducers and a 2-D planner array at the bottom of the cylinder.

FIG. 7 shows a cylindrical array scanner 110 having a cylindrical 2-D array 112a of transducers 16 in the inside surface of the cylinder wall 118 of the ultrasound transducer array. A planar array of elements 112b may also be positioned on the bottom surface 116 of the cylinder, which would primarily capture backscattered signals.

With the singular cylindrical array scanner 110, a first half of the semi-cylinder elements 16 will be opposed to or facing the second half of the semi-cylinder elements 16, and thus be positioned to receive direct transmission signals 30 (see FIG. 3) at least at varying degrees of angles of incidence. Thus depending on the amount of defocusing within each transducer, a plurality, or all, of the non-emitting transducers 16 will be able to receive a direct transmission signal 30 (FIG. 3) (at varying degrees) from the emitting transducer 16, leading to a full 3D ultrasound tomography image of the breast.

The top end 114 of the cylinder is open, such that the breast tissue 44 is immersed into the cylindrical array scanner 110 with 2D ultrasound transducer elements 16 surrounding the tissue 44. As with previous embodiments, the ultrasound transducer elements 16 can be in circular or rectangular shape, and the surface of the transducer element can be either flat or arc-shaped, as shown in FIG. 8 and FIG. 9.

D. Torroidal (Circular) Array Scanner

FIG. 10 shows a torroidal array scanner 120 having a circular array 122 of transducers 16 aligned in a ring that is configured to encircle the breast 44. A robotic stage 124 may be provided to allow for translation of the array 122 to and scan the breast 44 from the chest wall to the nipple region, slice by slice.

With the singular torroidal array scanner 120, a first half of the semi-circle elements 16 will be opposed to or facing the second half of the semi-circle elements 16, and thus be positioned to receive direct transmission signals 30 (see FIG. 3) at least at varying degrees of angles of incidence. Thus, depending on the amount of defocusing within each transducer, a plurality, or all, of the non-emitting transducers 16 will be able to receive a direct transmission signal 30 (at varying degrees) from the emitting transducer 16.

The circular array 122 preferably comprises defocused lens-transducer elements 16b as shown in FIG. 9, enabling 3-D breast ultrasound tomography. One advantage of the torroidal configuration 120 is using a fewer number of transducer elements compared to the cylindrical transducer array 110.

E. Dual Torroidal (Circular) Array Scanner

FIG. 11 shows another synthetic-aperture ultrasound breast tomography scanner 130 that incorporates use of two circular transducer arrays (upper circular array 132a and lower circular array 132b).

Image resolution depends, at least in part, on ultrasound illumination of the target medium 44. To increase the ultrasound out-of-plane illumination angle, an acoustic diverging lens 16b, as shown in FIG. 9, may be used to widen the elevation beam to the desired level (e.g. between points B and C in the upper circular array 132a and D and E in the lower circular array 132b (conically diverging beam)). Thus, the defocused ultrasound transducer elements 16b transmit ultrasound waves propagating not only to the transducer elements within the same circular array, e.g. between B and C in the upper ring 132a, but also to the other circular transducer array, e.g. between D and E in the lower ring 132b. The upper transducer array 132a may be configured to scan the breast 44 from the chest wall position to the nipple region. At each position, the lower transducer array 132b may move to different vertical position in the z-axis to acquire ultrasound data. This configuration leads to improved vertical resolution of breast ultrasound tomography images compared that obtained using one circular transducer array as shown in FIG. 10.

In practice, the two circular ultrasound transducer arrays 132a and 132b are immersed into the water tank 76 and both encircle the breast 44. One or both arrays 132a and 132b may be configured to translate vertically via a motorized stage 134. For example, during an ultrasound scan, the upper circular array 132a can be positioned against the chest wall, while the lower circular array 132b moves upward from below the nipple region, or vice versa.

As with previous embodiments, each element of one transducer array is fired sequentially, and all elements of both transducer arrays receive ultrasound scattering data 32. The scanner 130 acquires not only ultrasound propagating from one element to all elements within the same transducer array, but also those ultrasound waves propagating from the emitting element to all elements of the other transducer array, leading to a full 3D ultrasound tomography image of the breast.

Such a UST system 130 allows recording of volumetric ultrasound data, and the image resolution limited by slice thickness will be alleviated. In one exemplary design, the data acquisition electronics 18 allow a maximum of 768 parallel channels, so the number of transducers may be halved per array 132a and 132b. The coarser sampling in the plane of the array will be compensated by the cross illuminations The scanner 130 of FIG. 11 can significantly improve image resolution and quality compared to those obtained from an ultrasound tomography system with one circular transducer array. A 3D ultrasound tomography system 10 of this configuration will be operator independent, which is critical for cancer screening, and will be more cost-effective than an ultrasound tomography system with a cylindrical transducer array.

F. Combination 2D Planar and 2D-Arc Array Scanner

Figure 12:
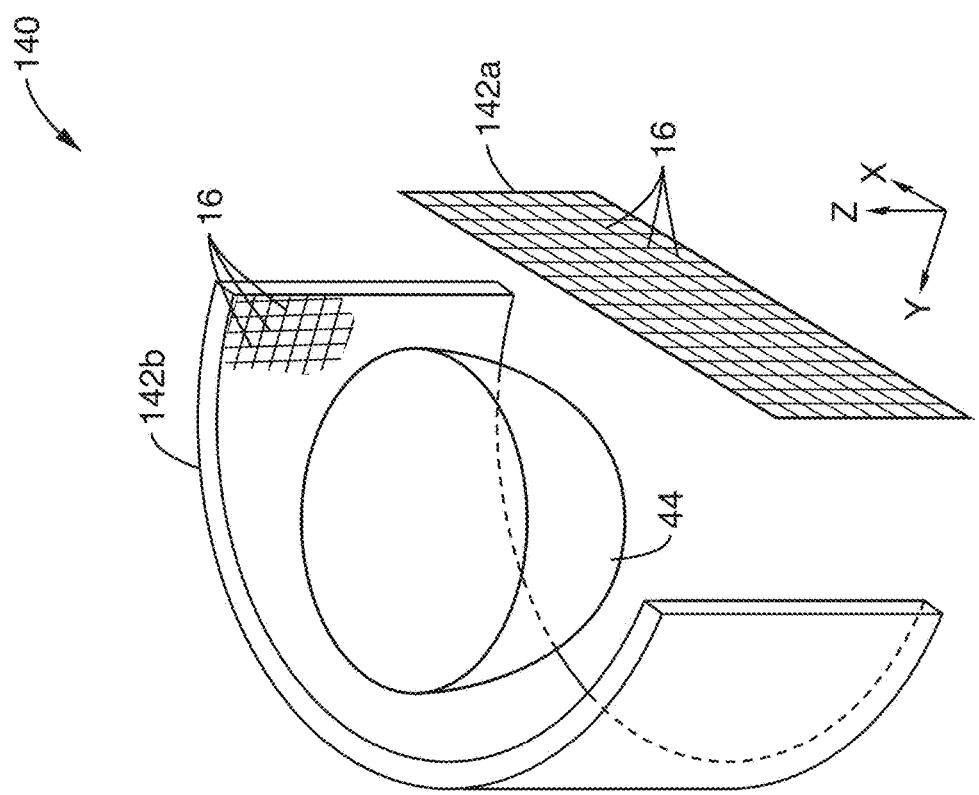
FIG. 12 shows a schematic view of a scanner comprising a semicircular or arcuate array having transducers in an opposing or facing orientation with planar array.

FIG. 12 shows a scanner 140 comprising a semicircular or arcuate array 142b having transducers 16 in an opposing or facing orientation with planar array 142a, with target tissue 44 disposed between the two. The scanner 140 provides a combination of the advantages of the cylindrical transducer array 110 with those of the 2D planner array 100. An ultrasound tomography system 10 with such combination of transducer arrays improves the range of spatial coverage for data acquisition, and the planar array 142 can still be placed near the axillary region.

G. Combination 1D Beam and Arc Array Scanner

Figure 13:
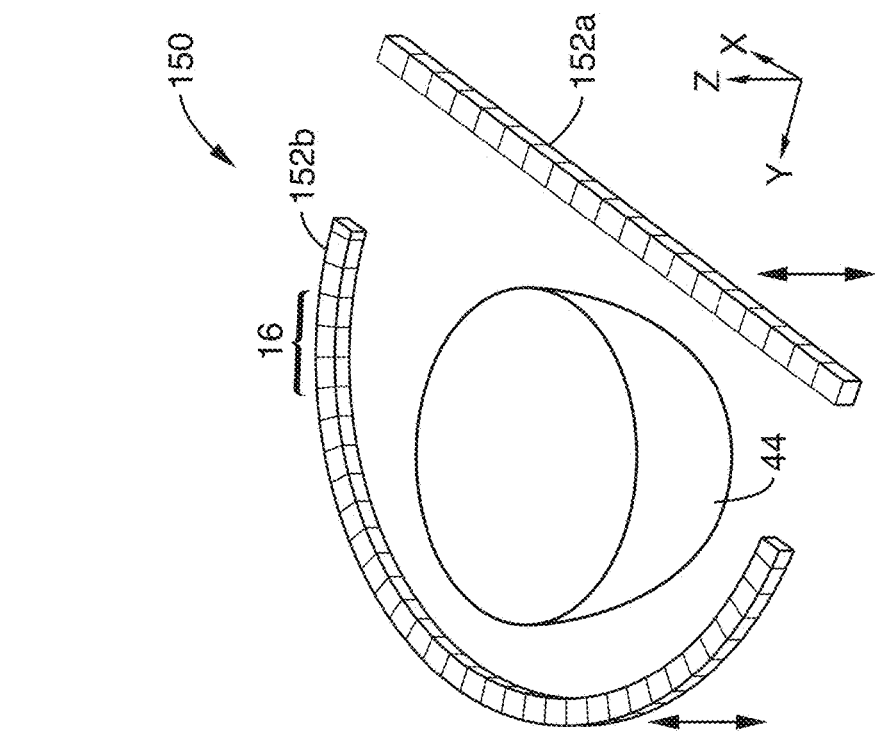
FIG. 13 illustrates a scanner that reduces the 2D arrays in FIG. 12 to 1D arrays.

FIG. 13 illustrates a scanner 150 that reduces the 2D arrays in FIG. 12 to 1D arrays (arcuate line array 152b and linear beam array 152a). This configuration, using a one-dimensional, straight-phased array 152a and a 1D arc-shaped array, 152 reduces the number transducers 16, and thus the number of channels required for data acquisition electronics 18, while improving the spatial coverage of data acquisition compared to when using a two parallel phased transducer array scanner 12 in FIG. 5.

II. Synthetic Aperture Ultrasound Tomography Methods

Figure 14:
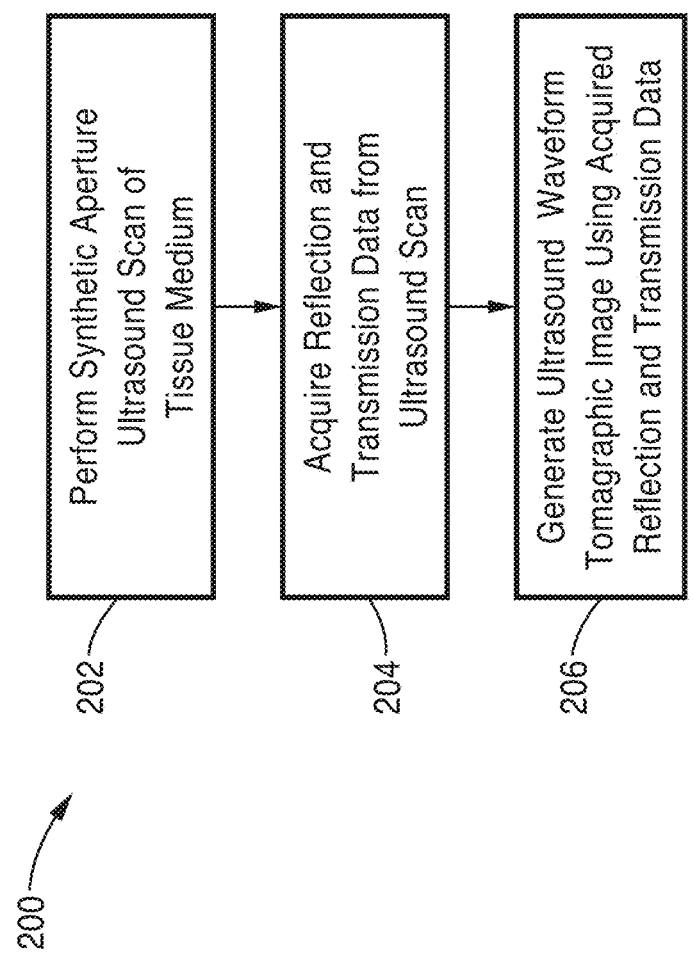
FIG. 14 is a flow diagram of a synthetic aperture ultrasound tomography method in accordance with the present invention.

Referring now to FIG. 14, a flow chart of a synthetic aperture ultrasound tomography method 200 is shown. This method is preferably used with any of the systems and scanners shown in FIG. 1 through FIG. 14, although other scanning systems are contemplated. Ideally, the method is used in conjunction with a scanner that has one or more arrays configured so that a plurality of transducers 16 of an array, or portion of an array, oppose (at a spaced-apart distance across the target scanning medium 44) a plurality of transducers 16 of either another portion of the array, or a separate array, so that reflection and transmission data may be acquired with each successive transducer excitation.

At step 202, the method performs a synthetic aperture ultrasound scan of the tissue medium in accordance with the schematic illustration of scanner 12 FIG. 3. At step 204, reflection and transmission data are simultaneously acquired, as shown in the method 50 of FIG. 4. At step 206, ultrasound waveform tomagraphic imaging is performed on the acquired reflection and transmission data to generate a high-resolution ultrasound reconstruction image of the target medium 44.

As mentioned previously, a particular shortcoming of existing ultrasound omographic imaging is that they either use only transmission data, or reflection data only, for image reconstructions. In contrast, the synthetic-aperture ultrasound tomography method 200 of the present invention acquired both ultrasound transmission and reflection data at the same time, and use both ultrasound transmission and reflection data for tomographic reconstructions to greatly improve the shapes and quantitative values of mechanical properties of abnormalities.

FIG. 15 through FIG. 18B demonstrate that using numerical breast-phantom data from ultrasound waveform tomography using both transmission and reflection data simultaneously significantly improves the accuracy of tomographic reconstructions, compared to those obtained using only ultrasound transmission data or only ultrasound reflection data.

Numerical phantom data was generated for a synthetic-aperture ultrasound tomography system with a two parallel phased transducer array scanner 12 as shown in FIG. 5. Each transducer array 14a, 14b is comprised of 384 evenly distributed ultrasound transducer elements, with a pitch size of 0.55 mm. The two transducer arrays were separated by 20 cm. The ultrasound source function used is a Ricker wavelet with a central frequency of 1.0 MHz.

Figure 15:
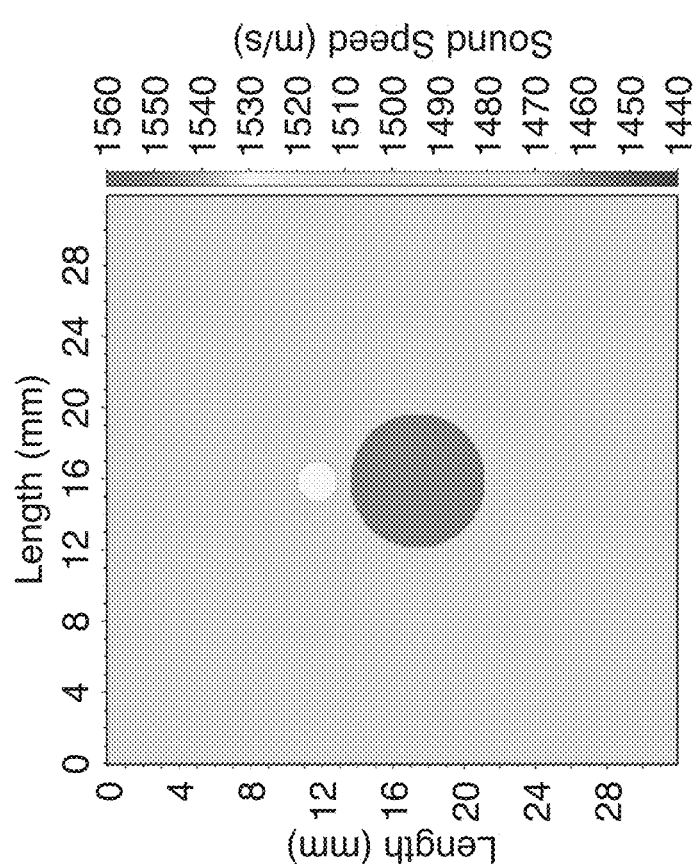
FIG. 15 shows an image of a numerical breast phantom containing two different tumors.

FIG. 15 shows an image of a numerical breast phantom containing two different tumors (small, light tumor, and larger dark tumor). The background sound-speed of the phantom was 1500 m/s, and those of the two tumor speeds were 1530 m/s and 1550 m/s, respectively. The diameters of the tumors were 2.0 mm and 7.0 mm, and approximately 1.3 wavelengths and 4.6 wavelengths. The two tumors were positioned along the longitudinal direction relative to the ultrasound transducer arrays. A high-order finite-difference time-domain wave-equation algorithm in accordance with step 206 was used to compute ultrasound transmission and reflection data.

Figure 16B:
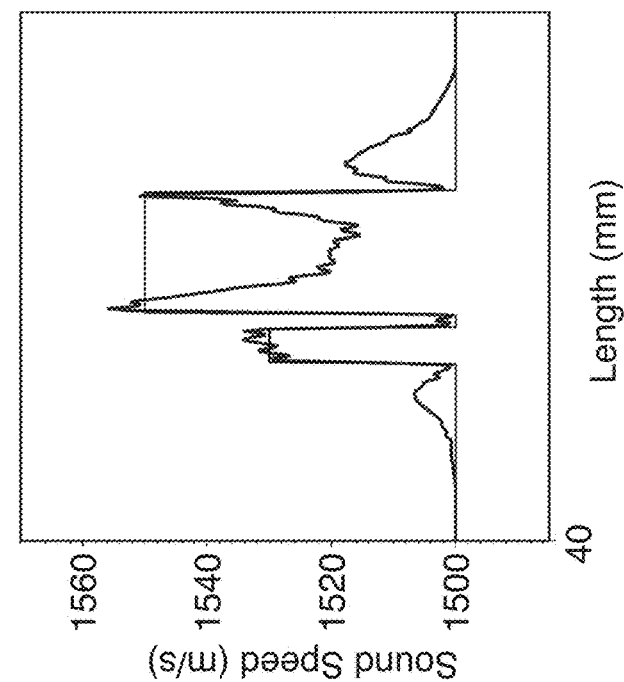
FIG. 16A and FIG. 16B show imaging results (tomographic reconstruction in FIG. 16A, and vertical profile along the center of the tumors in FIG. 16B) obtained using only the reflection data.
Figure 16A:
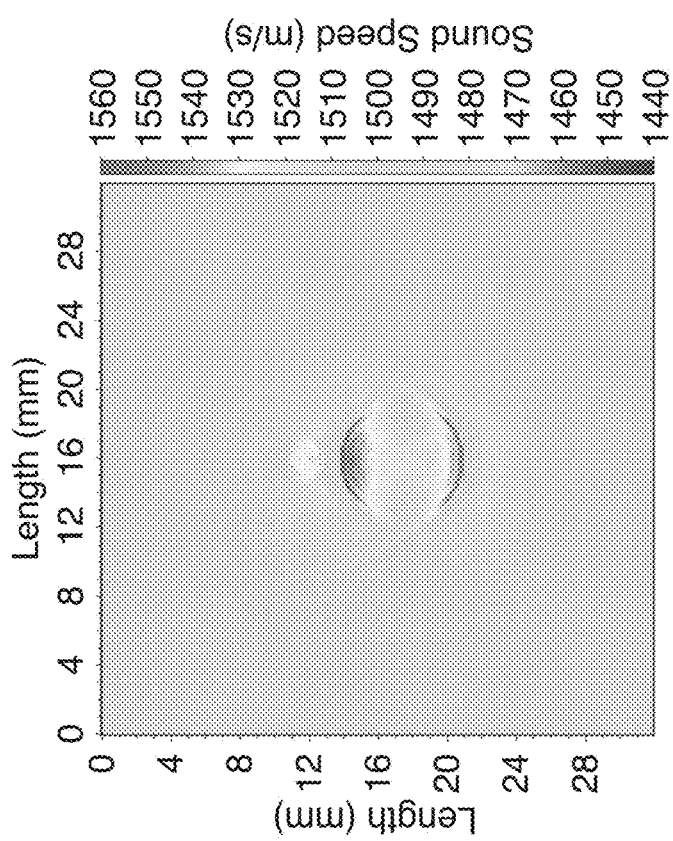
Figure 17B:
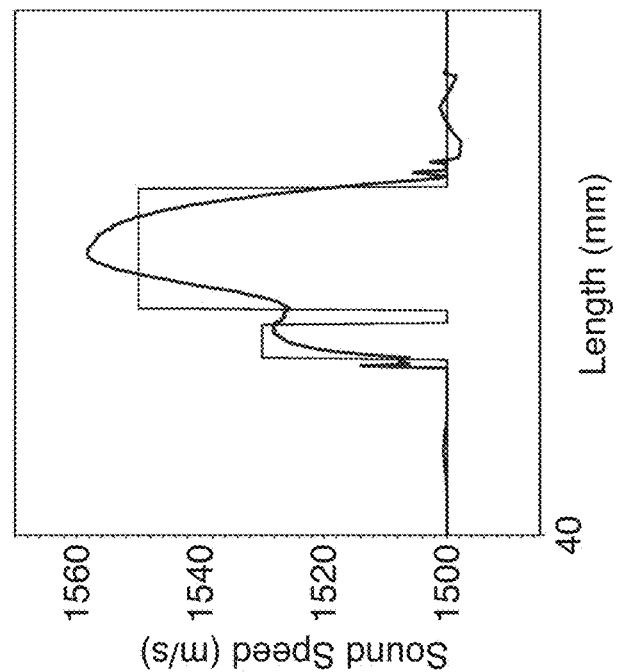
FIG. 17A and FIG. 17B show imaging results (tomographic reconstruction in FIG. 17A, and vertical profile along the center of the tumors in FIG. 17B) obtained using only the transmission data.
Figure 17A:
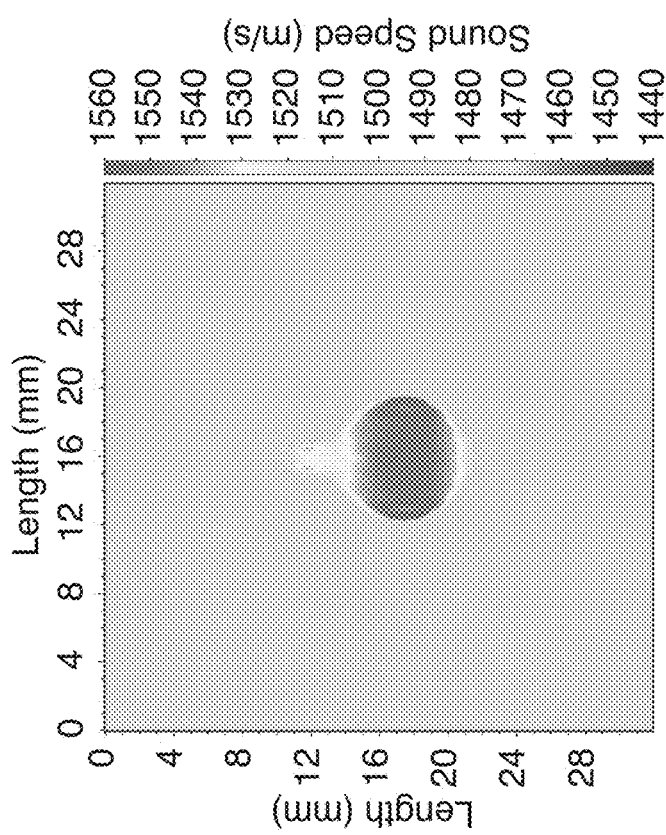
Figure 18B:
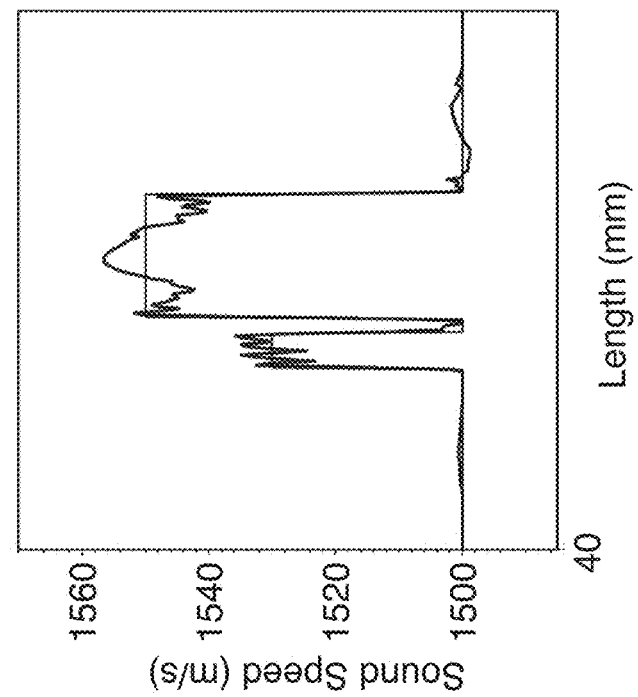
FIG. 18A and FIG. 18B show imaging results (tomographic reconstruction in FIG. 18A, and vertical profile along the center of the tumors in FIG. 18B) obtained using both transmission and reflection data simultaneously in accordance with method of the present invention.
Figure 18A:
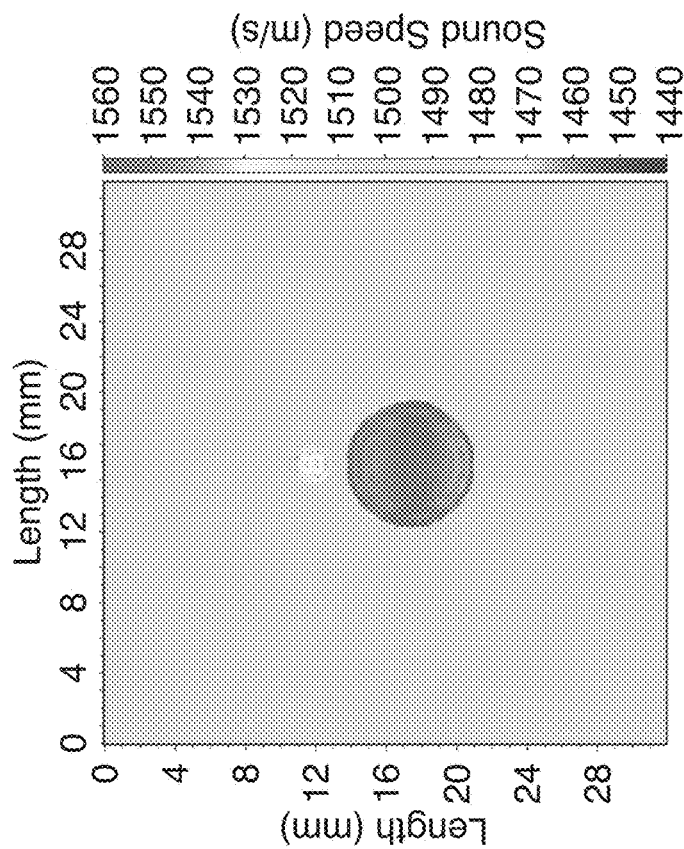

FIG. 16A and FIG. 16B show imaging results (tomographic reconstruction in FIG. 16A, and vertical profile along the center of the tumors in FIG. 16B) obtained using only the reflection data. FIG. 17A and FIG. 17B show imaging results (tomographic reconstruction in FIG. 17A, and vertical profile along the center of the tumors in FIG. 17B) obtained using only the transmission data. FIG. 18A and FIG. 18B show imaging results (tomographic reconstruction in FIG. 18A, and vertical profile along the center of the tumors in FIG. 18B) obtained using both transmission and reflection data simultaneously in accordance with method 200.

The waveform tomographic reconstruction using only the reflection data (FIG. 16A and FIG. 16B) provides mostly the edge information of the tumors, and can distinguish the two tumors.

On the other hand, the waveform tomographic reconstruction (FIG. 17A and FIG. 17B) using only the transmission data gives mostly low spatial-wavenumber components of the tumors, and it is almost impossible to separate the two tumors.

By contrast, the waveform tomographic reconstruction using both the transmission and reflection data simultaneously (FIG. 18A and FIG. 18B) takes the advantages of the above two kinds of tomographic reconstructions, and produces an image with much improved tumor edges and sound-speed reconstructions.

A. Synthetic Aperture Ultrasound Waveform Tomography

One aspect of the invention is a precondition approach to ultrasound waveform tomography without the need to calculate the Jacobin matrix. When computing the gradient using adjoint state techniques, both forward and backward wave propagations contain geometrical spreading effects. Therefore, it is straightforward to approximately remove the geometrical spreading effects by the wave energies of the forward and backward propagated wavefields. However, in the gradient calculation, the data residuals are back propagated. The backpropagated data residues not only contain the geometrical spreading effect, but also carry scattering information. Weighting the gradients using the wave energy of the backpropagated wavefield can alleviate the geometrical spreading effect, but can also undermine the focus of the backpropagated data residues to model perturbations. This weighting thus amplifies the artifacts around the perturbations, which can slow down the inversion process and may converge to a false solution.

The present invention is directed to a precondition approach to ultrasound waveform tomography using backpropagated synthetic wavefields from receivers and forward propagated wavefields from transmitting sources to scale the gradients. The method of the present invention removes the geometrical spreading effect and preserves the focus of the backpropagated data residues to model perturbations.

Ultrasound waveform tomography using both transmission and reflection data gives much better image reconstructions (higher resolution and better accuracy of sound-speed reconstructions) compared to ultrasound waveform tomography using only transmission data or only reflection data. When combining ultrasound reflection and transmission data for ultrasound waveform tomography, the amplitudes of transmission waves are much stronger than those of reflection waves, and have a dominant contribution to the gradients and reduce the convergence rate.

Figures 19, 20:
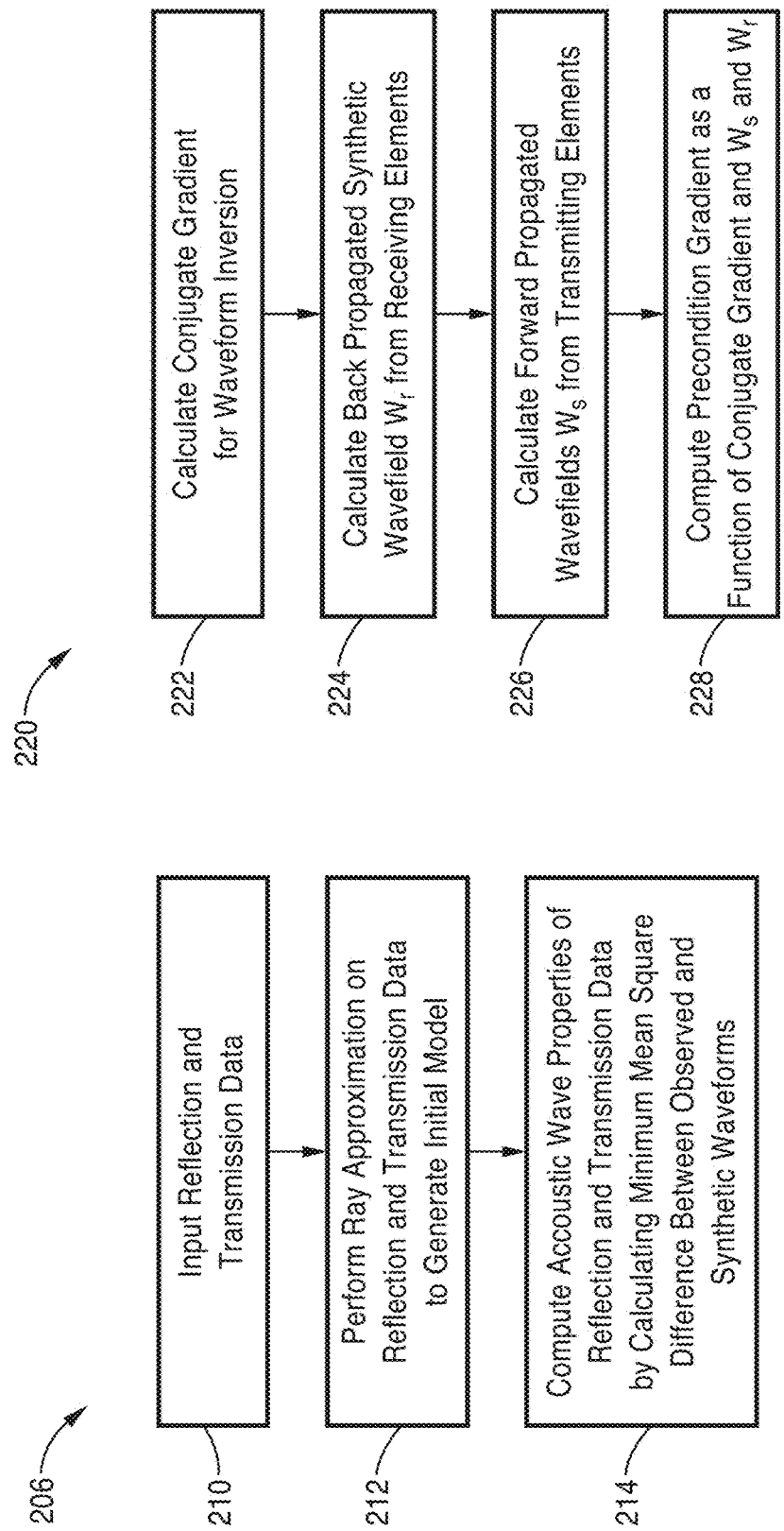
FIG. 19 illustrates a method using both transmission and reflection data for ultrasound waveform tomography.
FIG. 20 shows a wave-energy-based ultrasound waveform tomography precondition method in accordance with the present invention.

FIG. 19 illustrates a preferred method 206 for generating the ultrasound waveform step of method 200 (FIG. 14) using both transmission and reflection data for ultrasound waveform tomography. As shown in FIG. 19, reflection and transmission data are input at step 210, and ray approximation is performed at step 212 to generate an initial model. Next at step 214, image reconstruction is performed by computing the wave acoustic wave properties of the data by calculating the mean square difference between the observed and synthetic waveforms.

From a more basic level, performing step 214 is achieved by solving the acoustic wave equation of Eq. 1 with the minimization model of Eq. 2.

Ultrasonic-wave propagation is governed by the acoustic-wave equation in the time domain given by:

$$\left[\frac{1}{K(r)}\frac{\partial^2}{\partial t^2} - \nabla \cdot \left(\frac{1}{\rho(r)}\nabla\right)\right]p(r, t) = s(t)\delta(r - r_0), \qquad \text{Eq. 1}$$

where $\rho(r)$ is the density, $K(r)$ is the bulk modulus, $s(t)$ is the source term, $r_0$ is the source location, and $p(r,t)$ is the pressure field.

Ultrasound waveform tomography minimizes the misfit function given by:

$$E(m) = \min_m \left\{ \sum_{s=1}^{N_s} \|d_s - p_s(m)\|_2^2 \right\}, \qquad \text{Eq. 2}$$

where $E(m)$ is the misfit function, d represents the measured ultrasound wavefield, which can be either reflection data, or transmission data, or combined reflection and transmission data, p(m) is the simulated ultrasound wavefield, s is the emitting source index, $N_s$ is the number of sources, and m is the model parameter.

The wave-energy-based ultrasound waveform tomography precondition method 220 is shown in FIG. 20. From the input model, the method 220 first calculates the conjugate gradient for waveform inversion at step 222.

The gradient used in the conjugate gradient scheme for waveform inversion is given by:

$$\gamma = \tilde{A}^T \delta \tilde{d}, \qquad \text{Eq. 3}$$

and the Hessian matrix is given by:

$$H = \tilde{A}^T\tilde{A} + \left(\frac{\partial \tilde{A}}{\partial m}\right)^T \delta \tilde{d}, \quad \text{Eq. 4}$$

where m is the model parameter and $\delta\tilde{d}$=p−d.

If the bulk module is the model parameter and the density is constant, the Jacobin matrix $\tilde{A}$ in Eq. 4 is given by:

$$\tilde{A} = \sum_{(s,r)} \int_t \nabla \cdot g(x, x_r) \nabla \cdot p(x, s_s) dt, \quad \text{Eq. 5}$$

where g is the Green's function. The approximate Hessian is simply $H_a = \tilde{A}^T\tilde{A}$.

At step 224, the method 220 calculates the back propagated synthetic wavefield $W_r$ from all of the receiving elements, as well as the forward propagated wavefields $W_s$ from the transmitting elements (step 226).

If $P(x,x_s)$ set to be a discretized time series of $\nabla \cdot p(x,x_s)$, and $G(x,x_r)$ set to be a discretized time series of $\nabla \cdot g(x,x_r)$, then $W_s$ and $W_r$ can be defined as:

$$\begin{cases} W_s \equiv \sum_s P^T(x, x_s)P(x, x_s), \\ W_r \equiv \sum_r P^T G^T(x, x_r)G(x, x_r) p. \end{cases} \quad \text{Eq. 6}$$

With $W_s$ and $W_r$ known, the gradient is preconditioned at step 228 using:

$$\gamma_w = \frac{\tilde{A}^T \delta \tilde{d}}{\sqrt{W_s W_r}}. \quad \text{Eq. 7}$$

The precondition factor $\sqrt{W_s W_r}$ of the present invention is not an approximation of the diagonal terms of the approximate Hessian, because the diagonal terms of the approximate Hessian is given by:

$$\text{diag}\{\tilde{A}^T\tilde{A}\} = \quad \text{Eq. 8}$$
$$\left\{ \sum_{(s,r)} [P^T(x_1, x_s)G(x_1, x_r)]^2, \ldots, \sum_{(s,r)} [P^T(x_M, x_s)G(x_M, s_r)]^2 \right\}.$$

Compared with the conjugate gradient method, one additional simulation is needed to calculate $W_r$ in Eq. 6 for the wave-energy-based precondition scheme of the present invention for ultrasound waveform tomography.

$W_r$ is defined as:

$$W_r \equiv \sum_r \delta\tilde{d}^T G^T(x, x_r)G(x, x_r)\delta\tilde{d}, \quad \text{Eq. 9}$$

which is different from $W_r$ in equation Eq. 6.

The model is then updated along the search direction using the step length:

$$m^{(k+1)} = m^{(k)} + \alpha\gamma_w^{(k)}, \quad \text{Eq. 10}$$

where α is the step length. This process is repeated iteratively until a certain convergence criterion is satisfied.

Figure 21:
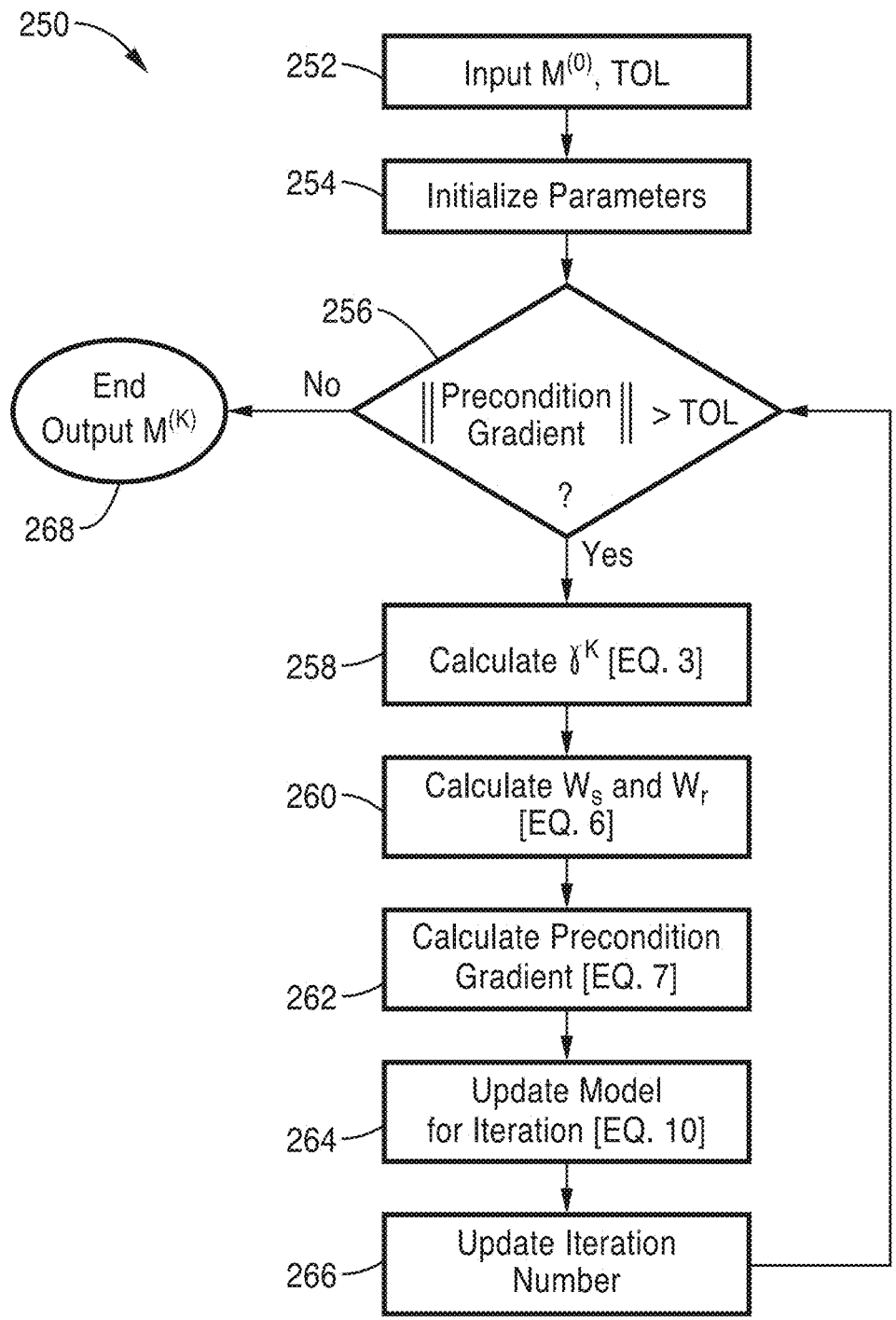
FIG. 21 is a flow diagram of an algorithm for a wave-energy-based ultrasound waveform tomography precondition method.

The wave-energy-based precondition method 250 for ultrasound waveform tomography is further detailed in the schematic flow diagram of FIG. 21, in addition to implementation within Algorithm 1 shown below.

The first step 252 in the method 250 is to input the specified tolerance TOL, in addition to the initial model $m^{(0)}$.

At step 254, the parameters are initialized (e.g. the current iteration value k is set at zero).

A step 256, the algorithm queries whether the current iteration of the precondition gradient has met the minimum value set by the assigned tolerance TOL.

If the threshold value has not been met, the algorithm calculates the conjugate gradient for waveform inversion by computing Eq. 3 at step 258.

Next, at step 260, Algorithm 1 calculates the back propagated synthetic wavefield $W_r$ from all of the receiving elements, as well the forward propagated wavefields $W_s$ from the transmitting elements via Eq. 6.

The precondition gradient $\gamma_w$ is then calculated at step 262 according to Eq. 7. At step 264 the current iteration model $m^{(k)}$ is updated based on step length and computed precondition gradient $\gamma_w$, as provided in Eq. 10.

The current iteration value k is then updated at step 266, and the process repeated at step 256.

If the threshold tolerance has been met at step 266, then the process ends, and outputs the model $m^{(k)}$ at step 268. If not, the loop continues to iterate until the threshold tolerance is met.

---

Algorithm 1 Ultrasound waveform tomography with a wave-energy-based precondition method

---

Input: $m^{(0)}$, TOL
Output: $m^{(k)}$
1: Initialize k = 0, $\gamma_w^{(0)}$;
2: while $\{||\gamma_w^{(k)}|| > \text{TOL}\}$ do
3:   Calculate $\gamma^{(k)}$ according to Eq. (3);
4:   Calculate $W_s$ and $W_s$ according to Eq. (6);
5:   Calculate $\gamma_w^{(k)}$ according to Eq. (7);
6:   Update model $m^{(k)}$ according to Eq.(10);
7:   k ← k + 1;
8: end while

---

The ultrasound waveform tomography method with wave-energy-based preconditioning scheme tested to a numerical breast phantom with spatial dimension of 70 mm×70 mm. The tomography system included an array of 236 transducer elements along two parallel phased-transducer arrays (see FIG. 5). Synthetic ultrasound transmission and reflection data from the 236 ultrasound transducer elements for a synthetic-aperture ultrasound tomography system with two parallel transducer arrays were generated using a finite-difference wave-equation algorithm.

Figures 22, 23:
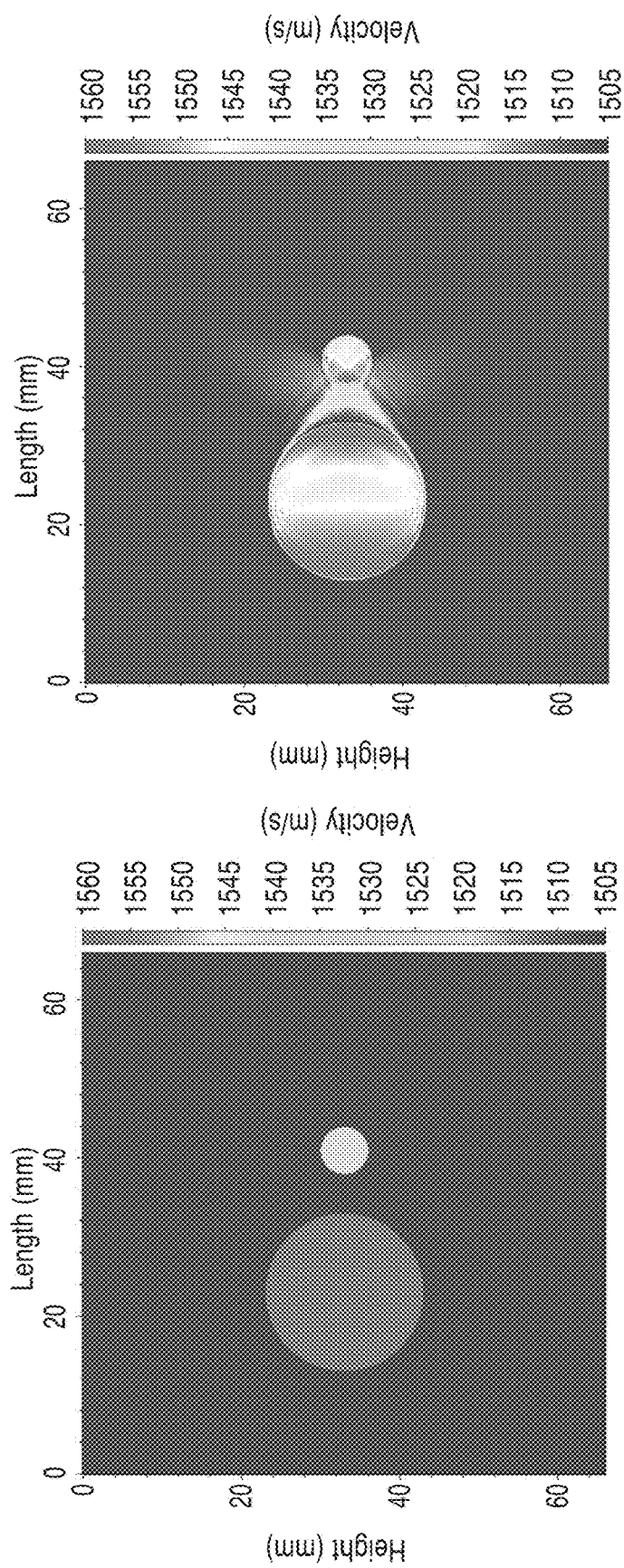
FIG. 22 is a numerical breast phantom contains two tumors with a diameter of 20 mm and 6 mm, respectively.
FIG. 23 is a reconstruction image of ultrasound waveform tomography with the conventional conjugate gradient method.
Figure 25:
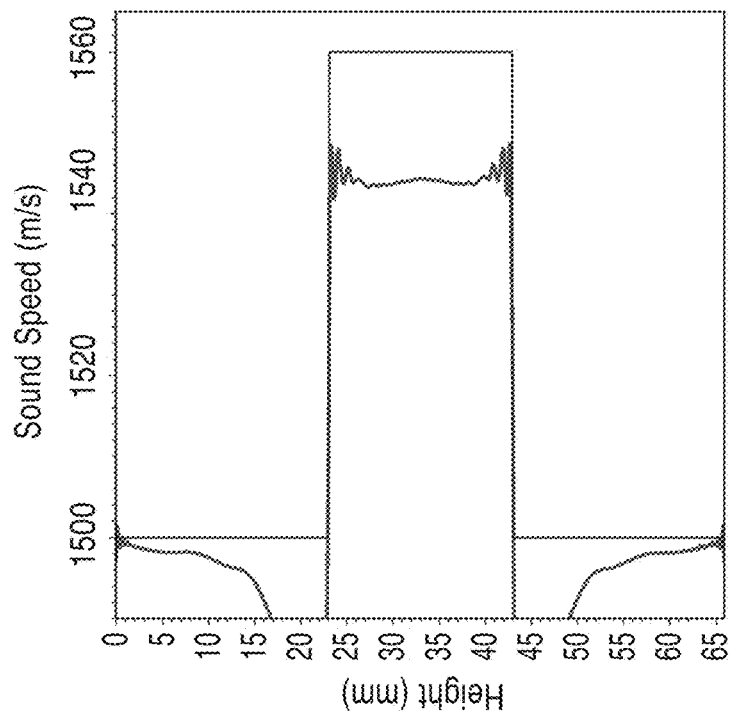
FIG. 25 shows a plot of the vertical profile of the reconstruction image at X=23 mm (across the large tumor) obtained using ultrasound waveform tomography with the conjugate gradient method.

Referring to FIG. 22, the numerical breast phantom contained two tumors with diameters 20 mm and 6 mm. The two tumors were positioned along the longitudinal direction relative to the two parallel phased transducer arrays. Simultaneous ultrasound transmission and reflection data was acquired to perform ultrasound waveform tomography.

FIG. 23 shows that ultrasound waveform tomography with the conventional conjugate gradient method reconstructs inaccurate values of the sound speeds of the tumors. In contrast, FIG. 24 demonstrates that ultrasound waveform tomography using the wave-energy-based precondition method 220 of the present invention accurately reconstructs the shapes of the sound-speed values of the two tumors. The image in FIG. 24 was obtained with two-thirds of the computational time needed to produce the image in the conventional approach of FIG. 23. This indicates that the ultrasound waveform tomography with the wave-energy-based precondition method converges much faster than methods using the conventional conjugate gradient method.

Figure 24:
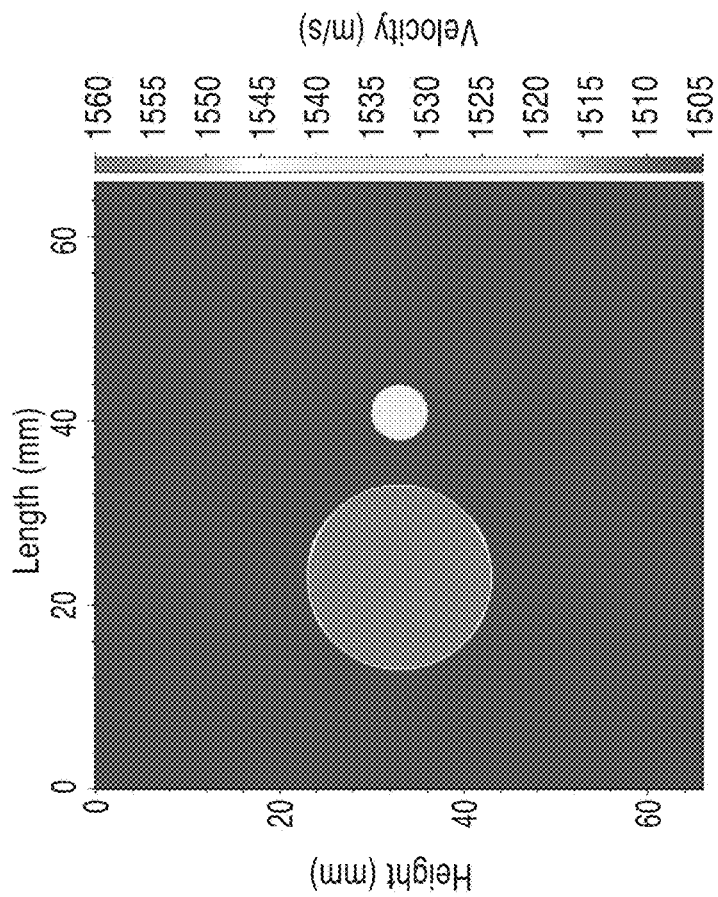
FIG. 24 shows a reconstruction image of ultrasound waveform tomography with the wave-energy-based precondition approach of the present invention.
Figure 27:
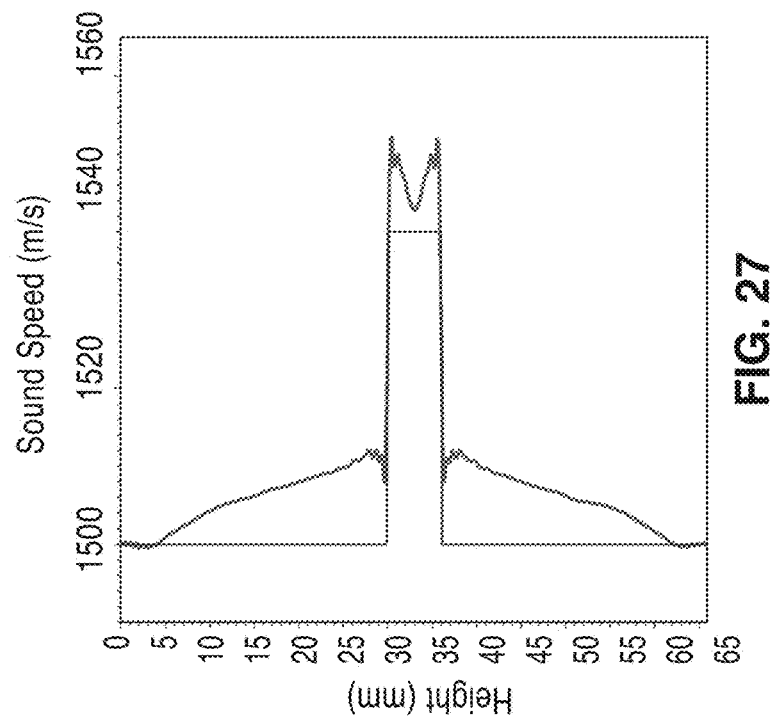
FIG. 27 is a plot of a vertical profile of the reconstruction image at X=41 mm (across the small tumor) obtained using ultrasound waveform tomography with the conjugate gradient method.
Figure 26:
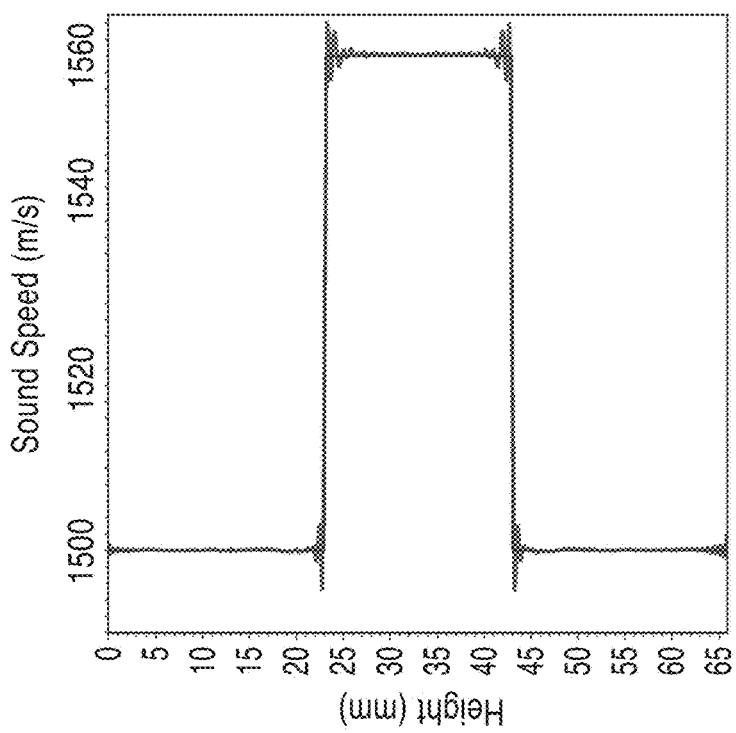
FIG. 26 is a plot of a vertical profile of the reconstruction image at X=23 mm (across the large tumor) obtained using ultrasound waveform tomography according to the wave-energy-based precondition method of the present invention.
Figure 29:
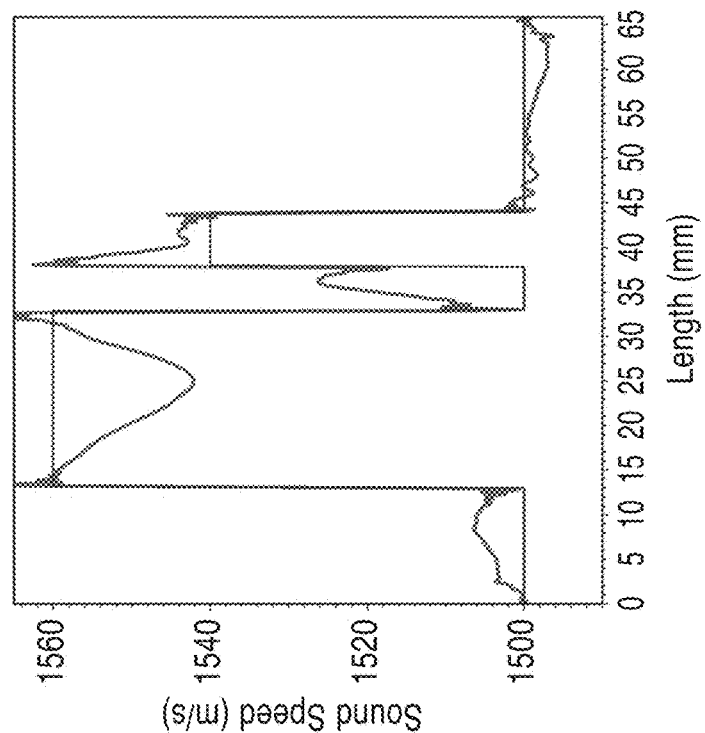
FIG. 29 is a horizontal profile of the reconstruction image at Y=33 mm obtained using ultrasound waveform tomography with the conjugate gradient method.
Figure 28:
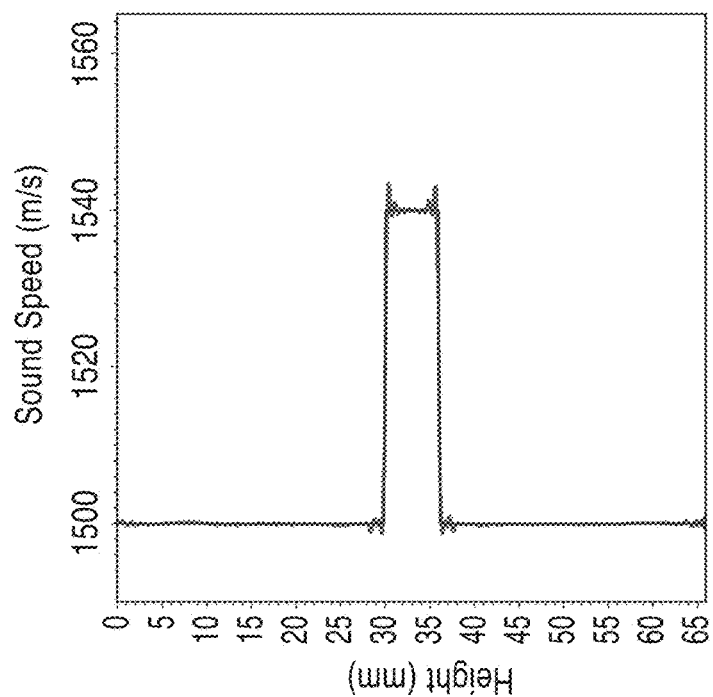
FIG. 28 shows a plot of a vertical profile of the reconstruction image at X=41 mm (across the small tumor) obtained using ultrasound waveform tomography with the wave-energy-based precondition method of the present invention.
Figure 30:
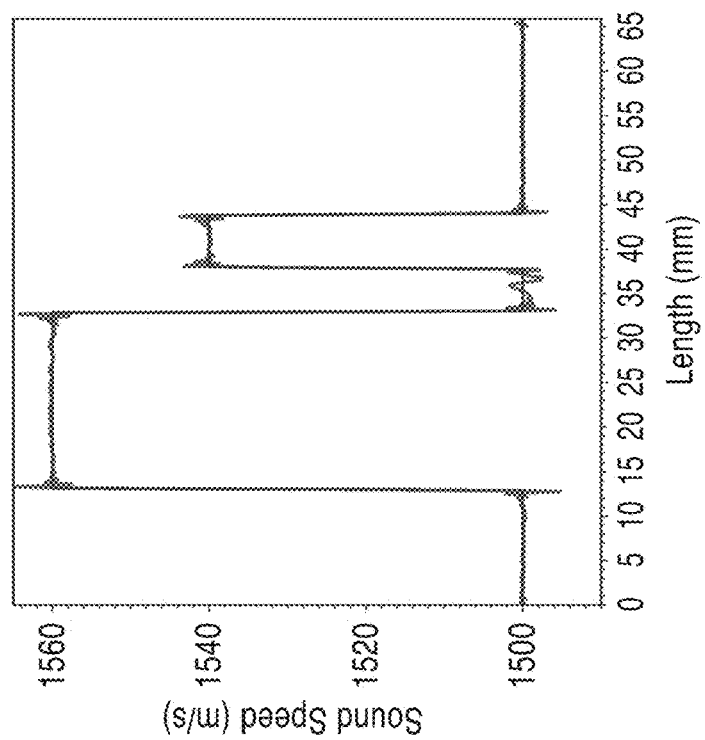
FIG. 30 is a horizontal profile of the reconstruction image at Y=33 mm obtained using ultrasound waveform tomography with the wave-energy-based precondition method of the present invention.

Vertical and horizontal profiles of the images in FIG. 23 and FIG. 24 were plotted to quantitatively compare their differences. The vertical profiles at X=23 mm and x=41 mm show that the sound speeds of the tumors are better reconstructed using the new wave-energy-weighted gradient method of the present invention (see FIG. 25, FIG. 26, FIG. 27, and FIG. 28). The horizontal profile at Y=33 mm shows similar improvement (see FIG. 29 and FIG. 30). Furthermore, our ultrasound waveform tomography with wave-energy-weighted gradients reconstructs the area between the two tumors in a much better manner.

Figure 31:
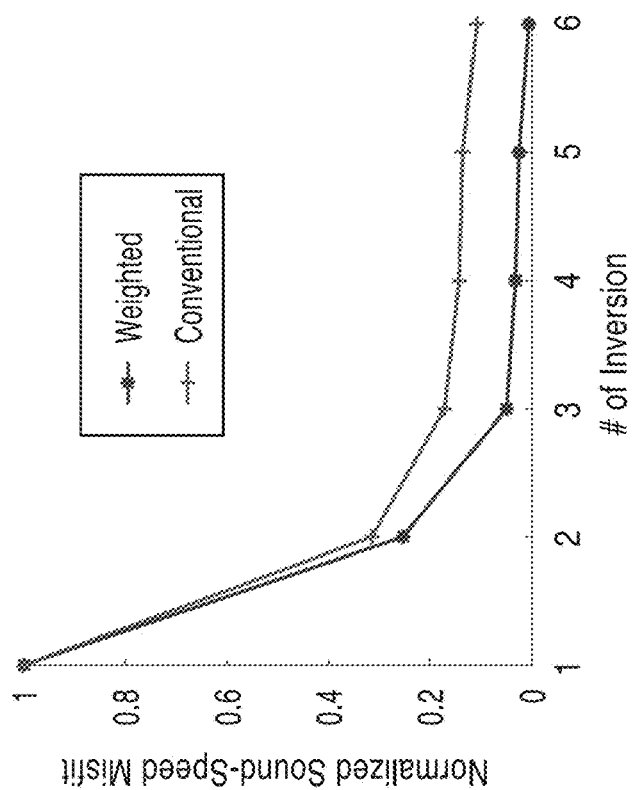
FIG. 31 shows a plot of the comparison of the convergence curve for an ultrasound waveform tomography method with the conventional conjugate gradient scheme (upper curve) with that for ultrasound waveform tomography with the wave-energy-based precondition approach of the present invention (lower curve). The latter method (lower curve) converges faster than the former method (upper curve).

The convergence curves in FIG. 31 demonstrate that the ultrasound waveform tomography with the wave-energy-based precondition method converges to the true model faster than ultrasound waveform tomography with the conventional conjugate gradient method.

In conclusion, a wave-energy-based precondition method for ultrasound waveform tomography was shown to improve image reconstructions and the convergence rate. The new precondition scheme retrieves the information included in the Hessian matrix, but not in the gradients. The scale factor used in the method of the present invention is not an approximation of the Hessian, or the diagonals of the Hessian. The wave-energy-based precondition method removes the propagation effects of ultrasound wavefields in the gradients. Meanwhile, by backpropagating synthetic waveforms from receivers, the method does not reduce the focusing of the data residue to model perturbations.

The wave-energy-based precondition method of the present invention uses one extra simulation for each source during each iteration, and therefore this method has a fractionally higher computation cost than ultrasound waveform tomography using a standard gradient-based method. On the other hand, ultrasound waveform tomography with the wave-energy-based precondition method converges much faster than that using the conventional gradient method, and consequently reduces the computational cost to some extent. The numerical examples demonstrate that the ultrasound waveform tomography with the wave-energy-based precondition method reconstructs the shapes and the sound speeds of breast tumors more accurately with fewer iteration steps than ultrasound waveform tomography with the conventional conjugate gradient method.

In summary, the synthetic-aperture ultrasound tomography systems and methods of the present invention acquire ultrasound transmission and reflection data at the same time, and we have demonstrated that ultrasound waveform tomography using both ultrasound transmission and reflection data simultaneously greatly improves tomographic reconstructions of shapes and sound-speeds of tumors compared to tomographic reconstructions using only transmission data or only reflection data.

From the discussion above it will be appreciated that the invention can be embodied in various ways, including the following:

1. An ultrasound tomography imaging system for imaging a tissue medium, the system comprising: one or more ultrasound transducer arrays; said one or more ultrasound transducer arrays comprising a plurality of ultrasound transducers; said plurality of transducers comprising transmitting source transducers for transmitting an ultrasound wavefield within the tissue medium and receiving transducers for receiving an ultrasound wavefield from the tissue medium; a processor; and programming executable on said processor and configured for: calculating back propagated synthetic wavefields from one or more receiving transducers; calculating forward propagated wavefields from one or more source transducers; and computing a precondition gradient as a function of the forward propagated wavefields and back propagated synthetic wavefields.

2. A system as recited in any of the preceding embodiments, wherein said programming is further configured for generating an ultrasound waveform tomographic image as a function of the precondition gradient.

3. A system as recited in any of the preceding embodiments, wherein the precondition gradient is not an approximation of diagonal terms of an approximate hessian associated with the wavefields.

4. A system as recited in any of the preceding embodiments, wherein said programming is further configured for: calculating a conjugate gradient from said wavefields; wherein the precondition gradient is a function of the forward propagated wavefields and back propagated synthetic wavefields.

5. A system as recited in any of the preceding embodiments, wherein said programming is further configured for: exciting a first transducer with plurality of transducers to generate an ultrasound field within the tissue medium; receiving a transmission signal and a reflection signal from a second transducer within the one or more ultrasound transducer arrays; and generating an ultrasound waveform tomography image reconstruction using both the acquired reflection and transmission signals and the precondition gradient.

6. A system as recited in any of the preceding embodiments, wherein said programming is further configured for simultaneously receiving the reflection and transmission signals from the second set of two or more transducers.

7. A synthetic aperture ultrasound tomography imaging method for imaging a tissue medium with one or more ultrasound transducer arrays comprising a plurality of receiving transducers and source transducers, the method comprising: exciting a first transducer with plurality of transducers to generate an ultrasound field within the tissue medium; receiving a transmission signal and a reflection signal from a second transducer within the one or more ultrasound transducer arrays; calculating back propagated synthetic wavefields from one or more receiving transducers; calculating forward propagated wavefields from one or more source transducers; computing a precondition gradient as a function of the forward propagated wavefields and back propagated synthetic wavefields; and generating an ultrasound waveform tomography image reconstruction using both the acquired reflection and transmission signals and the precondition gradient.

8. A method as recited in any of the preceding embodiments, wherein generating an ultrasound waveform tomography image reconstruction is a function of computing an acoustic wave property of the reflection and transmission signals by calculating a minimum mean square difference between observed and synthetic waveforms relating to the reflection and transmission signals.

9. A method as recited in any of the preceding embodiments, wherein the image reconstruction is a function of:

$$E(m) = \min_{m}\{\|d - f(m)\|_2^2\},$$

where $\|d-f(m)\|_2^2$ comprises a misfit function, and d comprises data relating to the acquired reflection signal and transmission signal.

10. A method as recited in any of the preceding embodiments: wherein the plurality of transducers are configured such that a first set of two or more transducers are positioned at an opposing spaced-apart orientation from a second set of two or more transducers such that the first set of two or more transducers face the second set of two or more transducers; wherein the first and second sets of two or more transducers are positioned at spaced-apart locations so as to allow for the tissue medium to be positioned in between the first and second sets of two or more transducers; and wherein said method further comprises: exciting a first transducer with the first set of two or more transducers to generate an ultrasound field within the tissue medium; and receiving a transmission signal and a reflection signal from at least the second set of two or more transducers.

11. A method as recited in any of the preceding embodiments, further comprising: receiving a reflection signal from all transducers in the one or more arrays.

12. A method as recited in any of the preceding embodiments, further comprising simultaneously receiving the reflection and transmission signals from the second set of two or more transducers.

13. A synthetic aperture ultrasound tomography imaging system for imaging a tissue medium with one or more ultrasound transducer arrays comprising a plurality of receiving transducers and source transducers, the system comprising: a processor; and programming executable on said processor and configured for: exciting a first transducer with plurality of transducers to generate an ultrasound field within the tissue medium; receiving a transmission signal and a reflection signal from a second transducer within the one or more ultrasound transducer arrays; and calculating back propagated synthetic wavefields from one or more receiving transducers; calculating forward propagated wavefields from one or more source transducers; computing a precondition gradient as a function of the forward propagated wavefields and back propagated synthetic wavefields; and generating an ultrasound waveform tomography image reconstruction using both the acquired reflection and transmission signals and the precondition gradient.

14. A system as recited in any of the preceding embodiments, wherein said step of generating an ultrasound waveform tomography image reconstruction is a function of computing an acoustic wave property of the reflection and transmission signals by calculating a minimum mean square difference between observed and synthetic waveforms relating to the reflection and transmission signals.

15. A system as recited in any of the preceding embodiments 14, wherein the image reconstruction is a function of:

$$E(m) = \min_m \{\|d - f(m)\|_2^2\},$$

where $\|d-f(m)\|_2^2$ comprises a misfit function, and d comprises data relating to the acquired reflection signal and transmission signal.

16. A system as recited in any of the preceding embodiments: wherein the plurality of transducers are configured such that a first set of two or more transducers are positioned at an opposing spaced-apart orientation from a second set of two or more transducers such that the first set of two or more transducers face the second set of two or more transducers; wherein the first and second sets of two or more transducers are positioned at spaced-apart locations so as to allow for the tissue medium to be positioned in between the first and second sets of two or more transducers; and wherein said programming is further configured for: exciting a first transducer with the first set of two or more transducers to generate an ultrasound field within the tissue medium; and receiving a transmission signal and a reflection signal from at least the second set of two or more transducers.

17. A system as recited in any of the preceding embodiments, wherein said programming is further configured for receiving a reflection signal from all transducers in the one or more arrays.

18. A system as recited in any of the preceding embodiments, wherein said programming is further configured for simultaneously receiving the reflection and transmission signals from the second set of two or more transducers.

19. A system as recited in any of the preceding embodiments, wherein the precondition gradient is not an approximation of diagonal terms of an approximate hessian associated with the wavefields.

20. A system as recited in any of the preceding embodiments, wherein said programming is further configured for: calculating a conjugate gradient from said wavefields; wherein the precondition gradient is a function of the forward propagated wavefields and back propagated synthetic wavefields.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic.

As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula (e), or computational depiction(s).

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An ultrasound tomography Imaging system for imaging a tissue medium, the system comprising:
   one or more ultrasound transducer arrays;
   said one or more ultrasound transducer arrays comprising a plurality of ultrasound transducers;
   said plurality of transducers comprising transmitting source transducers for transmitting an ultrasound wavefield within the tissue medium and receiving transducers for receiving an ultrasound wavefield from the tissue medium;
   a processor; and
   programming executable on said processor and configured for:
      calculating back propagated synthetic wavefields from one or more of the receiving transducers;
      calculating forward propagated wavefields from one or more of the transmitting source transducers;
      computing a precondition gradient as a function of a product of the forward propagated wavefields and back propagated synthetic wavefields; and
      generating an ultrasound waveform tomographic image as a function of the precondition gradient,
   wherein the precondition gradient is a function of a square root of the product of the forward propagated wavefields and the back propagated synthetic wavefields.

2. A system as recited in claim 1, wherein the precondition gradient is not an approximation of diagonal terms of an approximate Hessian associated with the wavefields.

3. A system as recited in claim 1, wherein said programming is further configured for calculating a conjugate gradient from said wavefields.

4. A system as recited in claim 1, wherein said programming is further configured for:
   exciting a first transducer of the plurality of transducers to generate the ultrasound wavefield within the tissue medium; and
   receiving a transmission signal and a reflection signal from a second transducer within the one or more ultrasound transducer arrays,
   wherein the generating the ultrasound waveform tomography Image comprises using both the acquired reflection and transmission signals, and
   wherein the back propagated synthetic wavefields are calculated using the acquired reflection signals and the forward propagated wavefields are calculated using the transmission signals.

5. A system as recited in claim 4, wherein said programming is further configured for simultaneously receiving the reflection and transmission signals from the second transducer.

6. A synthetic aperture ultrasound tomography imaging method for imaging a tissue medium with one or more ultrasound transducer arrays comprising a plurality of receiving transducers and source transducers, the method comprising:
   exciting a first transducer of the plurality of source transducers to generate an ultrasound field within the tissue medium;
   receiving a transmission signal and a reflection signal from a second transducer of the plurality of receiving transducers
   calculating back propagated synthetic wavefields from one or more of the receiving transducers;
   calculating forward propagated wavefields from one or more of the source transducers;
   computing a precondition gradient as a function of a product of the forward propagated wavefields and back propagated synthetic wavefields; and
   generating an ultrasound waveform tomography image reconstruction using both the acquired reflection and transmission signals and the precondition gradient,
   wherein the precondition gradient is a function of a square root of the product of the forward propagated wavefields and the back propagated synthetic wavefields.

7. A method as recited in claim 6, wherein the generating an ultrasound waveform tomography image reconstruction is a function of:

$$E(m) = \min_{m}\{\|d - f(m)\|_2^2\},$$

where $\|d-f(m)\|_2^2$ comprises a misfit function, and d comprises data relating to the acquired reflection signal and transmission signal.

8. A method as recited in claim 6:
   wherein the plurality of transducers are configured such that the source transducers are positioned at an opposing spaced-apart orientation from the receiving transducers such that the source transducers face the receiving transducers; and
   wherein the source and receiving transducers are positioned at spaced-apart locations so as to allow for the tissue medium to be positioned in between the source and receiving transducers.

9. A method as recited in claim 8, further comprising:
receiving the reflection signal from all transducers in the one or more arrays.

10. A method as recited in claim 9, further comprising simultaneously receiving the reflection and transmission signals from the receiving transducers.

11. A synthetic aperture ultrasound tomography imaging system for imaging a tissue medium with one or more ultrasound transducer arrays comprising a plurality of receiving transducers and source transducers, the system comprising:

a processor; and
programming executable on said processor and configured for:
exciting a first transducer of the plurality of source transducers to generate an ultrasound field within the tissue medium;
receiving a transmission signal and a reflection signal from a second transducer of the plurality of receiving transducers;
calculating back propagated synthetic wavefields from one or more of the receiving transducers;
calculating forward propagated wavefields from one or more of the source transducers;
computing a precondition gradient as a function of a product of the forward propagated wavefields and back propagated synthetic wavefields; and
generating an ultrasound waveform tomography image reconstruction using both the acquired reflection and transmission signals and the precondition gradient,
wherein the precondition gradient is a function of a square root of the product of the forward propagated wavefields and the back propagated synthetic wavefields.

12. A system as recited in claim 11, wherein the generating an ultrasound waveform tomography image reconstruction is a function of:

$$E(m) = \min_{m}\{\|d - f(m)\|_2^2\},$$

where $\|d-f(m)\|_2^2$ comprises a misfit function, and d comprises data relating to the acquired reflection signal and transmission signal.

13. A system as recited in claim 11:
wherein the plurality of transducers are configured such that the source transducers are positioned at an opposing spaced-apart orientation from the receiving transducers such that the source transducers face the receiving transducers; and
wherein the source and receiving transducers are positioned at spaced-apart locations so as to allow for the tissue medium to be positioned in between the source and receiving transducers.

14. A system as recited in claim 13, wherein said programming is further configured for receiving the reflection signal from all transducers in the one or more arrays.

15. A system as recited in claim 14, wherein said programming is further configured for simultaneously receiving the reflection and transmission signals from the receiving transducers.

16. A system as recited in claim 11, wherein the precondition gradient is not an approximation of diagonal terms of an approximate Hessian associated with the wavefields.

17. A system as recited in claim 11, wherein said programming is further configured for calculating a conjugate gradient from said wavefields.

* * * * *